(12) United States Patent
Yeung et al.

(10) Patent No.: US 6,387,234 B1
(45) Date of Patent: May 14, 2002

(54) INTEGRATED MULTIPLEXED CAPILLARY ELECTROPHORESIS SYSTEM

(75) Inventors: Edward S. Yeung; Hongdong Tan, both of Ames, IA (US)

(73) Assignee: Iowa State University Research Foundation, Inc., Ames, IA (US)

(*) Notice: Subject to any disclaimer, the term of this patent is extended or adjusted under 35 U.S.C. 154(b) by 0 days.

(21) Appl. No.: 09/144,170

(22) Filed: Aug. 31, 1998

(51) Int. Cl.$^7$ .............................................. G01N 27/26
(52) U.S. Cl. .................. 204/451; 204/601; 204/602; 422/70
(58) Field of Search .................. 137/828, 827, 137/251.1, 341, 13; 204/602, 451, 601; 422/70; 240/656

(56) References Cited

U.S. PATENT DOCUMENTS

| | | | |
|---|---|---|---|
| 5,006,210 A | 4/1991 | Yeung et al. ................ 204/452 |
| 5,582,705 A | 12/1996 | Yeung et al. ................ 204/603 |
| 5,667,972 A | 9/1997 | Drmanac et al. ............. 435/6 |
| 5,695,626 A | 12/1997 | Yeung et al. ................ 204/605 |
| 5,695,940 A | 12/1997 | Drmanac et al. ............. 435/6 |
| 5,741,411 A | 4/1998 | Yeung et al. ................ 204/452 |
| 5,795,788 A | * 8/1998 | Bevan et al. ................ 436/161 |
| 5,935,522 A | * 8/1999 | Swerdlow et al. ........... 422/70 |
| 5,988,197 A | * 11/1999 | Colin et al. .................... 137/13 |

FOREIGN PATENT DOCUMENTS

| WO | WO 89/10977 | 11/1989 |
|---|---|---|
| WO | WO 99/67693 A1 | 12/1999 |

OTHER PUBLICATIONS

T. Anazawa et al., "A Capillary Array Gel Electrophoresis System Using Multiple Laser Focusing for DNA Sequencing," *Anal. Chem.* 68:2699–2704 (Aug. 1996).

P. J. Barr et al., "7–Deaza–2'–Deoxyguanosine– 5'–Triphosphate: Enhanced Resolution in M13 Dideoxy Sequencing," *BioTechniques* 4:428–432 (1986). Month unavailable.

C. D. Bevan et al., "Freeze–Thaw Flow Management: A Novel Concept for High–Performance Liquid Chromatography, Capillary Electrophoresis, Electrochromatography and Associated Techniques," *J. Chromatogr. A.*, 697:541–548 (1995). Month unavailable.

C. D. Bevan et al., "Use of Freeze–Thaw Flow Management for Controlling and Switching Fluid Flow in Capillary Tubes," *Anal. Chem.*, 67:1470–1473 (Apr. 1995).

R. L. Chien et al., "On–Column Sample Concentration Using Field Amplification in CZE, " *Anal. Chem.* 64:489A–496A (Apr. 1992).

L. M. Davis et al., "Rapid DNA Sequencing Based Upon Single Molecule Detection," *Genet. Anal.* 8:1–7 (1991). Month unavailable.

(List continued on next page.)

*Primary Examiner*—Jill Warden
*Assistant Examiner*—Alex Noguerola
(74) *Attorney, Agent, or Firm*—Mueting, Raasch & Gebhardt, P.A.

(57) ABSTRACT

The present invention provides an integrated multiplexed capillary electrophoresis system for the analysis of sample analytes. The system integrates and automates multiple components, such as chromatographic columns and separation capillaries, and further provides a detector for the detection of analytes eluting from the separation capillaries. The system employs multiplexed freeze/thaw valves to manage fluid flow and sample movement. The system is computer controlled and is capable of processing samples through reaction, purification, denaturation, preconcentration, injection, separation and detection in parallel fashion. Methods employing the system of the invention are also provided.

46 Claims, 10 Drawing Sheets

OTHER PUBLICATIONS

Q. Gao et al., "A Matrix for DNA Separation: Genotyping and Sequencing Using Poly(vinylprrolidone) Solution in Uncoated Capillaries," *Anal. Chem.* 70:1382–1388 (Apr. 1998).

P. M. Goodwin et al., "Application of Single Molecule Detection to DNA Sequencing," *Nucleosides & Nucleotides* 16:543–547 (1997). Month unavailable.

A. Guttman et al., "Artifacts Related to Sample Introduction in Capillary Gel Electrophoresis Affecting Separation Performance and Quantification," *Anal. Chem.* 67:2279–2283 (Jul. 1995).

X. C. Huang et al., "Cappillary Array Electrophoresis Using Laser–Excited Confocal Fluorescence Detection," *Anal. Chem.* 64:967–972 (1992).

P. Juhasz et al., "Applications of Delayed Extraction Matrix– Assisted Laser Desorption Ionization Time–of––Flight Mass Spectrometry to Oligonucleotide Analysis," *Anal. Chem.* 68:941–946 (1993). Month unavailable.

A. V. Lemmo et al., "Transverse Flow Gating Interface for the Coupling of Microcolumn LC with CZE in a Comprehensive Two–Dimensional System," *Anal. Chem.*, 65:1576–1581 (1993). Month unavailable.

X. Lu et al., "Optimization of Excitation and Detection Geomety for Multiplexed Capillary Array Electrophoresis of DNA Fragments," *Appl. Spectrosc.* 49:605–609 (1995), Month unavailable.

R.S. Madabhushi et al., "Separation of 4–Color DNA Sequencing Extension Products in Noncovalently Coated Capillaries Using Low Viscosity Polymer Solutions," *Electrophoresis* 19:224–230 (1998), Month unavailable.

E. R. Mardis et al., "Automated Methods for Single–Stranded DNA Isolation and Dideoxynucleotide DNA Sequencing Reactions on a Robotic Workstation," *Bio Techniques* 7:840–850 (1989), month unavailable.

S.Mizusawa et al., "Improvement of the dideoxy Chain Termination Method of DNA Sequencing by Use of Deoxy–7–Deazaguanosine Triphosphate in Place of dGTP," *Nucl. Acids Res.* 14:1319–1324 (Feb. 1986).

O. Salas–Solano et al., "Rugged Separation of More than 1000 DNA Sequencing Fragments in Less than 1 Hour by Capillary Electrophoresis Using Mixed LPA Polymer Solutions," *Eleventh International Symposium on High Performance Capillary Electrophoresis and Related Microscale Techniques*, Abstract P547, (1998). Month unavailable.

H. Swerdlow et al., "Rapid Cycle Sequencing in an Air Thermal Cycler," *BioTechniques* 512–519 (1993). month unavailable.

H. Swerdlow et al., "Fully Automated DNA Reaction and Analysis in a Fluidic Capillary Instrument," *Anal. Chem.* 69:848–855 (Mar. 1997). month unavailable.

H. Tan et al., "Integrated On–Line System for DNA Sequencing by Capillary Electrophoresis: Form Template to Called Bases," *Anal. Chem.* 69:664–674 (Feb. 1997).

H. Tan et al., "Multiplexed Integrated On–Line System for DNA Sequencing by Capillary Electrophoresis: From Template to Called Bases," poster, U.S. Dept. of Energy Human Genome Project Contractor—Grantee Workshop, Santa Fe, NM (Nov. 9, 1997).

U.S. Dept. of Energy and Health, "A Five–Year Plan for the U.S. Human Genome Project," *Science* 262:43–46 (Oct. 1993).

R. K. Wilson et al., "Automation of Dideoxynucleotide DNA Sequencing Reactions Using a Robotic Workstations," *Bio Techniques* 6:776–777 (1988).

A. T. Woolley et al., "Ultra–High–Speed DNA Fragment Separations Using Microfabricated Capillary Array Electrophoresis Chips," *Proc. Natl. Acad. Sci. (USA)* 91:11348–11352 (1994).

A. T. Woolley et al., "Ultra–High–Speed DNA Sequencing Using Capillary Electrophoresis Chips," *Anal. Chem.* 67:3676–3680 (Oct. 1995).

A. T. Woolley et al., "Functional Integration of PCR Amplification and Capillary Electrophoresis in a Microfabricated DNA Analysis Device," *Anal. Chem.* 68:4081–4086 (Dec. 1996).

E. Yeung et al., "Multiplexed Integrated On–Line System for DNA Sequencing by Capillary Electrophoresis: From Template to Called Bases," (abstract) U.S. Dept. of Energy Human Genome Project Contractor—Grantee Workshop, Santa Fe, NM (Nov. 9–13, 1997).

N. Zhang et al., "On–Line Coupling of Polymerase Chain Reaction and Capillary Electrophoresis for Automatic DNA Typing and HIV–1 Diagnosis," *Eleventh International Symposium on High Performance Capillary Electrophoresis and Related Microscale Techniques,* Abstract P548, (1998). Month unavailable.

* cited by examiner

INTEGRATED MULTIPLEXED CAPILLARY ELECTROPHORESIS SYSTEM

GOVERNMENT RIGHTS

This invention was made with government support under Contract No. W-7405-Eng-82, awarded by the U.S. Department of Energy. The government has certain rights in this invention.

BACKGROUND OF THE INVENTION

The demand for quick and efficient analysis of biochemical and chemical analytes continues to be an area of great interest in the medical and scientific community. For example, from its inception, the Human Genome Project (U.S. Dept. of Energy and Health, *Science* 262:43–46 (1993)) has called upon existing technologies to provide cost-effective, high-speed and high-throughput nucleic acid sequencing. This was necessary primarily because of the inadequate overall efficiency of traditional slab gel electrophoresis techniques. Alternative technologies, such as capillary array electrophoresis (Huang et al., *Anal. Chem.* 64:967–972 (1992)), microchannel array electrophoresis (Woolley et al., *Proc. Natl. Acad. Sci. (USA)* 91:11348–11352 (1994); Woolley et al., *Anal. Chem.* 67:3676–3680 (1995)), sequencing by hybridization (Drmanac et al., Yugoslav Patent Application 570 (1987); GB 8810400 (1988)), single-molecule sequencing (Davis et al., *Genet. Anal.* 8:1–7 (1991); Goodwin et al., *Nucleosides & Nucleotides* 16:543–547 (1997)), and sequencing by mass spectroscopy (Juhasz et al., *Anal. Chem.* 68:941–946 (1996)) have been explored extensively. Intensive research efforts have also been directed toward improving the individual technologies, such as reaction chemistry, purification, sample injection, separation, detection, and data analysis. Ultimately, integration and automation of the above-described technologies will be critical to the success of the Human Genome Project.

Capillary electrophoresis (CE) is an attractive alternative to conventional slab gel electrophoresis in nucleic acid analysis due to advantages such as high migration speed, high separation efficiency, small sample requirement, and suitability for automation. For example, CE greatly improves nucleic acid sequencing rates compared to conventional slab gel electrophoresis. However, capillary electrophoresis and conventional slab gel technologies have yet to be interfaced with sample processing technologies in a multiplexed system. System integration of CE to robotic arms and conveyer-belts (Mardis et al., *BioTechniques* 7:840–850 (1989); Wilson et al., *BioTechniques* 6:776–777 (1988)), although workable, suffers from reliability and incompatibility issues because of the many moving parts at the robotic end and the small volumes at the separation and detection end. On the other hand, on-line integrated microfluidics is inherently more compatible with the capillary/microchannel formats. Based on this approach, DNA restriction digestion (Woolley et al., *Anal. Chem.* 68:4081–4086 (1996)), polymerase chain reaction (Swerdlow et al., *Anal. Chem.* 69:848–855 (1997)), and cycle sequencing reaction (Tan et al., *Anal. Chem.* 69:664–674 (1997)), have all been interfaced with capillary/microchannel electrophoresis for sizing. Although these studies successfully coupled sample preparation with separation and detection in a single channel, multiplexing of these elements has not been demonstrated.

It has been previously shown that an on-line integrated microfluidic system from dye-terminator sequencing reaction to called bases is feasible in a single channel (Tan et al., *Anal. Chem.* 69:664–674 (1997)). This was accomplished by identifying a set of compatible and automatable technologies. In this system, a fused-silica capillary served as the microreactor of cycle-sequencing reaction inside a hot-air thermal cycler. A mini-bore chromatographic column based on size exclusion was used to purify the reaction products. A cross-shaped junction, i.e., a 4-way junction, acted as a multi-functional device for denaturation, pre-concentration, and injection at a high temperature. CE coupled with laser-induced fluorescence was utilized to read the DNA sequence. One of the major obstacles toward multiplexing this approach, however, was the inclusion of four bulky rotary valves. Most of the traditional mechanical valves, whether they are linear valves (gate, globe, diaphragm, or pinch) or rotary valves (ball, plug, butterfly, or shaft), are not suitable for constructing a highly parallel system. Although electro-osmotic flow control represents an available alternative, it is not compatible with the use of a purification column. Furthermore, it is unreliable under changing buffer conditions, which are necessitated by complex manipulations.

Thus, a need exists for an integrated multiplexed on-line system capable of simultaneously analyzing multiple samples. The multiplexed system should provide greater efficacy over conventional procedures with regard to time and further improve the efficiency of separation, purification and detection of analytes contained within the samples.

SUMMARY OF THE INVENTION

The present invention provides an advancement in the processing of samples based upon multiplexed microfluidics and capillary array electrophoresis. A system of the invention can process multiple samples and if desired, execute multiple sample manipulation steps, preferably all in a parallel fashion. In one embodiment, the system can contain a plurality of intake capillaries, a chromatographic column array having a plurality of chromatographic columns and a separation capillary array having a plurality of separation capillaries. At least one detector can be integrated into the system to detect analytes eluting from the separation capillaries and/or the chromatographic columns. In another embodiment, the system contains a plurality of intake capillaries each having a reaction portion and a separation capillary array having a plurality of separation capillaries.

A system of the invention typically employs at least one multiplexed freeze-thaw valve assembly (MFTV) that regulates the flow of fluids in the system. Valve assemblies are positioned in a system in a manner that allows sample movement through the integrated components in automated fashion. Sample and fluid movement in the system are typically controlled by a series of valves and pumps that are activated by an electronic signal from a computer. A system of the invention typically contains at least one set of junctions and at least one manifold that permits fluid communication between selected integrated components in the system. A multiplexed system of the invention can advantageously support two sample analysis channels to about one thousand or ore sample analysis channels.

In a first embodiment, the system contains a plurality of intake capillaries, each intake capillary in fluid communication with one of a plurality of first junctions; a chromatographic column array containing a plurality of chromatographic columns having an outlet end, each chromatographic column in fluid communication with one of the plurality of first junctions and one of a plurality of second junctions, the chromatographic column being interposed between the first and second junctions; and a separation capillary array containing a plurality of separation capillaries, each separation capillary in fluid communication with one of the plurality of second junctions and having an outlet end.

In another embodiment, the system contains a plurality of intake capillaries, each intake capillary having a reaction portion for reacting a sample, wherein each intake capillary is in fluid communication with one of a plurality of junctions; and a separation capillary array containing a plurality of separation capillaries, each separation capillary in fluid communication with one of the plurality of junctions and having an outlet end.

The invention further provides at least one multiplexed freeze thaw valve assembly containing a plurality of capillaries, at least a portion of each capillary containing a fluid, and a plurality of heat conductive portions in contact with the fluid-containing portions of the plurality of capillaries; wherein the valve assembly is closed by contacting the heat conductive portions with a cooled liquid to solidify the fluid in the capillaries.

The various methods provided by the present invention include a method for detecting an analyte in at least one sample. Once such method includes the steps of (a) providing a plurality of intake capillaries, each intake capillary having an inlet end and in fluid communication with one of a plurality of first junctions; a chromatographic column array containing a plurality of chromatographic columns having an outlet end, each chromatographic column in fluid communication with one of the plurality of first junctions and one of a plurality of second junctions, the chromatographic column being interposed between the first and second junctions; and a separation capillary array containing a plurality of separation capillaries, each separation capillary in fluid communication with one of the plurality of second junctions and having a distal portion with an outlet end; (b) introducing each of the plurality of samples into the inlet end of an intake capillary; (c) transferring each of the plurality of samples from each intake capillary into a chromatographic column in fluid communication with each of the intake capillaries; (d) chromatographing each of the plurality of samples to yield a plurality of purified sample portions, the purified sample portions comprising at least one detectable analyte; (e) injecting each of the plurality of purified sample portions into a separation capillary in fluid communication with the chromatographic column; (f) separating each of the purified sample portions to yield a plurality of separated sample portions, each of the separated sample portions comprising at least one detectable analyte; and (g) detecting at least one detectable analyte.

Another method includes the steps of: (a) providing a plurality of intake capillaries, having an inlet end in fluid communication with a plurality of junctions, wherein each intake capillary is formed to have a reaction portion; a separation capillary array containing a plurality of separation capillaries, each separation capillary in fluid communication with one of the plurality of junctions and having an outlet end; (b) introducing each of the plurality of samples into inlet end of an intake capillary and transferring each of the plurality of samples into the reaction portion of each intake capillary; (c) reacting each of the transferred samples to yield a reacted sample; (d) injecting each of the plurality of reacted samples into a separation capillary in fluid communication each of the intake capillaries; (e) separating each of the reacted samples to yield a plurality of separated sample portions, each of the separated sample portions comprising at least one detectable analyte; and (f) detecting at least one detectable analyte.

Yet another method provides for sequencing nucleic acids in a plurality of samples that contains the steps of: (a) providing a plurality of intake capillaries, each intake capillary in fluid communication with one of a plurality of first junctions, wherein at least one intake capillary has a reaction portion for reacting a sample; a chromatographic column array containing a plurality of chromatographic columns having an outlet end, each chromatographic column in fluid communication with one of the plurality of first junctions and one of a plurality of second junctions, the chromatographic column being interposed between the first and second junctions; a separation capillary array containing a plurality of separation capillaries, each separation capillary in fluid communication with one of the plurality of second junctions and having an outlet end; a plurality of first freeze-thaw valves for regulating the flow of fluids in the system, each first freeze-thaw valve containing a portion of an intake capillary wherein each of the plurality of first freeze-thaw valves contains a distal freeze thaw valve having a portion of the intake capillary distal to the reaction portion and a proximal freeze-thaw valve having a portion of the intake capillary proximal to the reaction portion; a plurality of first joining capillaries, each first joining capillary interposed between a first junction and a chromatographic column, the first junction being in fluid communication with the intake capillary; a plurality of second freeze-thaw valves for regulating the flow of fluids in the system, each second freeze-thaw containing a portion of a first joining capillary; (b) introducing each of the plurality of samples into the reaction portion of an intake capillary, each sample containing a nucleic acid; (c) reacting each of the plurality of samples in a DNA sequencing reaction to yield a plurality of reacted samples, each reacted sample containing a plurality of detectably labeled nucleic acid fragments having different lengths; (d) transferring each of the plurality of reacted samples from each of the intake capillaries into the chromatographic column in fluid communication with the intake capillary; (e) chromatographing each of the plurality of reacted samples to yield a plurality of purified samples, each purified sample containing a plurality of detectably labeled nucleic acid fragments having different lengths; (f) injecting each of the plurality of purified samples into a separation capillary in fluid communication with the chromatographic column; (g) separating each of the plurality of purified samples to yield, for each purified sample, a plurality of separated detectably labeled nucleic acid fragments having different lengths; (h) detecting the detectably labeled nucleic acid fragments having different lengths; and (i) for each sample, determining the sequence of the nucleic acid.

DETAILED DESCRIPTION OF PREFERRED EMBODIMENTS

The present invention provides an integrated multiplexed system that allows automatic, high speed, high accuracy, and low cost analysis of charged or neutral analytes contained within one or more samples. The apparatus of the invention integrates sample processing technologies with multiplexed capillary electrophoresis allowing sample processing, separation, and detection of sample components for multiple samples in a single experiment. The system is based upon multiplexed microfluidics, is amenable to computer control, and provides automatic operation and system regeneration. As discussed in greater detail below, operation of the integrated multiplexed system involves introducing at least one sample into a plurality of intake capillaries; processing the sample, for example, by introducing the sample into a chromatographic column array and initiating chromatographic separation of the sample to yield a purified sample; a subsequent injection of the purified sample into a separation capillary array; and detecting at least one separated analyte from the sample. Conveniently, regeneration of the intake capillaries, the chromatographic column array, and the separation capillary array can occur after each sample run or be performed concurrently with system operation.

A "sample," as used herein, can be a native or untreated sample, a chemically or biologically pre-treated or reacted sample, or a reaction mixture of a native sample and one or more added components useful in the analysis of the sample. As used herein, the term "analyte" or "analytes" refer to detectable constituents and/or detectable target species in a sample. The term "target species," as used herein, refers to a particular detectable constituent or detectable in the sample. Target species are typically flourescent target species. A "reacted sample," as used herein, is typically a sample that has been modified or altered by either a chemical or biological process. For example, a sample can be modified or altered by a nucleic acid sequencing reaction, such as a labeled terminator cycle sequencing reaction. Optionally, heat can be employed to initiate or catalyze the reaction.

Additionally, although the multiplexed system of the invention suggests several sample processing components that can be integrated with separation capillary electrophoresis, any on-line component useful in pre-separation manipulations can be utilized. Thus, the invention is not to be to limited to the specific pre-separation system components described herein, such as chromatographic columns.

Figure 1:
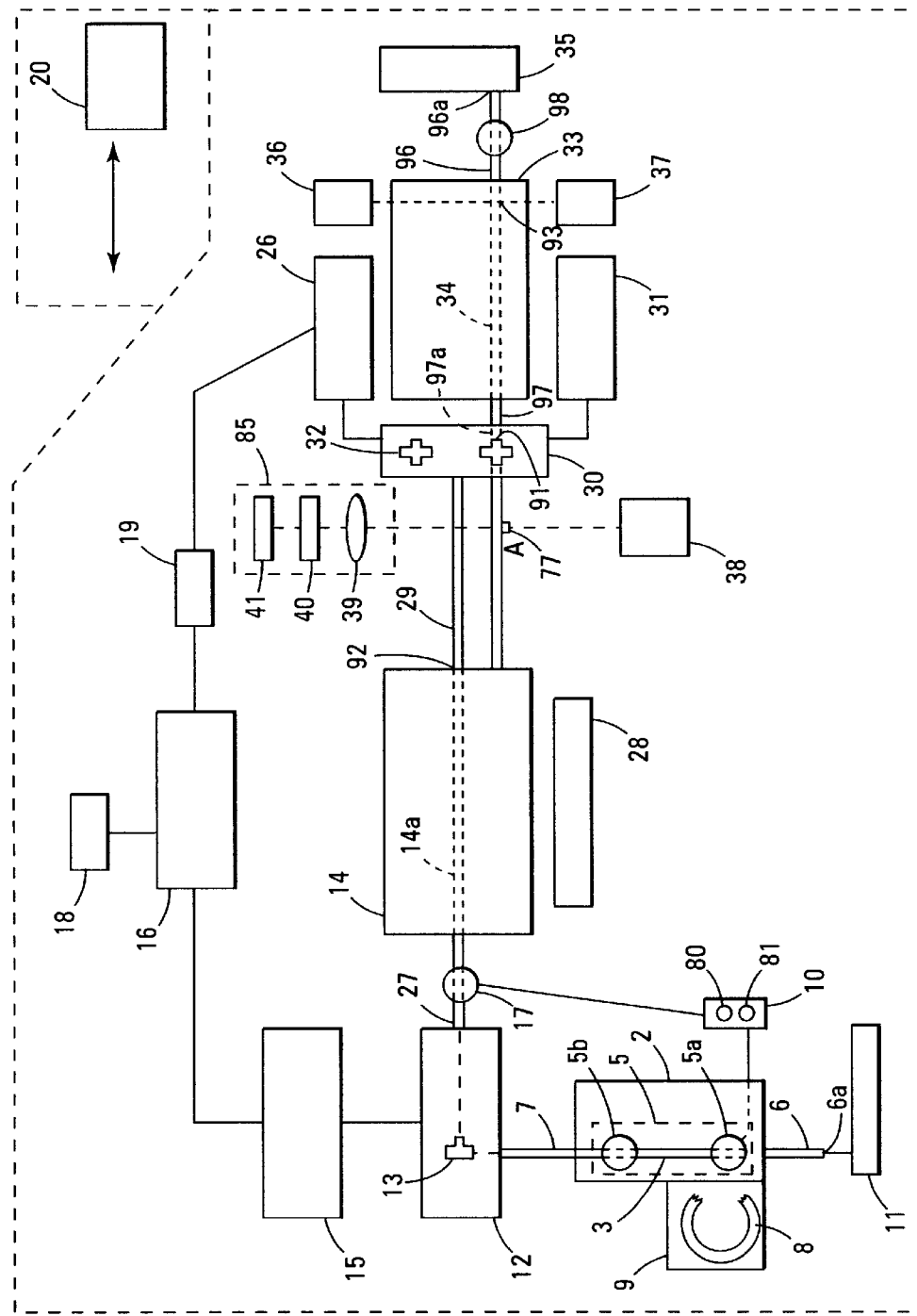
FIG. 1 is a block diagram of the integrated multiplexed system of the invention.

FIG. 1 provides an overview of the integrated multiplexed apparatus 1 of the invention. At least one sample containing at least one analyte is loaded into the system by a delivery device 11 holding the sample. By computer initiated control of pump 18 and valves 16 using computer 20, sample(s) are introduced into a plurality of intake capillaries 3 and pumped through the intake capillaries 3 by fluid control of a plurality of first multiplexed freeze thaw valves (MFTVs) 5 controlled by solenoid valves 10. Each of a plurality of first MFTVs 5 contain at least a portion of an intake capillary 3. Each of the intake capillaries 3 can optionally contain a reaction portion 8 that can further be optionally housed in a heater assembly 9. The sample(s) are subsequently introduced into a first manifold 15 through a T-assembly 12. The first manifold 15 functions as a means to deliver system buffers and reagents during operation, and further provides a small region for sample loading prior to introduction into a chromatographic column array 14. The T-assembly 12 contains a plurality of first junctions 13 that connect the intake capillaries 3 with a plurality of first joining capillaries 27. Sample(s) are subsequently pumped into the plurality of first joining capillaries 27 by fluid control of a plurality of second MFTVs 17 and the plurality of first MFTVs 5. Each of a plurality of second MFTVs 17 contain at least a portion of a first joining capillary 27.

Sample(s) are pumped through a first plurality of joining capillaries 27 which connect the T-assembly 12 with the chromatographic column array 14 having individual chromatographic columns 14a, wherein each chromatographic column has an outlet end 92. Sample(s) are chromatographed by the chromatographic columns 14a of the chromatographic column array 14 to yield purified sample portion(s). A sample or sample portion is "purified" in that it is essentially free or substantially free from non-detectable or non-targeted analyte materials or species. Optionally, one or more of the chromatographic columns 14a in the chromatographic column array 14 can be heated by a water bath 28.

A plurality of second joining capillaries 29, each comprising a detection window 77, are connected to each of the chromatographic columns 14a and to a cross-assembly 30 which has a plurality of second junctions 32. Each second junction 32 further has an injection region 91. The cross-assembly 30, by means of the second plurality of junctions 32, is additionally connected to a second manifold 26, a third manifold 31, and a separation capillary array 33. The second manifold 26 and the third manifold 31, as discussed more fully below, permit separate buffer flows to individual separation capillaries 34 in a separation capillary array 33, and collect waste from the individual chromatographic columns 14a. Purified sample(s) are pumped through the plurality of second joining capillaries 29 passing by an optional first detector 85. Detector 85 is optional in that it will typically be employed in a system utilizing, for example, at least one chromatographic column 14a in a chromatographic column array 14. A coherent light source 38 is positioned at the detection window 77 of at least one of the joining capillaries 29 of the plurality of second joining capillaries 29. The first detector 85 can comprise a lens 39, an objective 40, and a photomultiplier tube 41. Alternatively, the detector can comprise a charge-coupled device (CCD) or a charge-injection device (CID).

Purified sample(s) are subsequently positioned at the injection region 91 of second junctions 32 and the separation capillary array 33. The separation capillary array 33 contains a plurality of individual separation capillaries 34. Each separation capillary 34 has a transparent window portion 93, and, relative to the cross assembly 30, a distal portion 96 having an outlet end 96a, and a proximal portion 97 having an inlet end 97a. An electrokinetic injection of the purified sample(s) into each separation capillary 34 is accomplished by using a syringe pump 19. Separation of the sample(s), by either electrophoresis or pressure flow, yields at least one analyte in the sample(s) that is detectable by a second detector 36 and includes a coherent light source 37. The distal portion 96 of each separation capillary 34 terminates in a buffer reservoir 35. As shown, in FIG. 3, buffer reservoir 35 represents a positive end of the potential in capillary electrophoresis.

Optionally, and as discussed more fully below in a discussion of the MFTVs, a third MFTV assembly 98, positioned at the distal portion 96 of the individual separation capillaries 34, can be employed. This third MFTV assembly 98 can be utilized to stop fluid flow in the separation capillaries 34 in several applications. For example, this can be used in a gel electrophoresis application where a low viscosity polymer matrix is employed, or in zone-electrophoresis where no matrix is employed. In the application employing a low viscosity matrix, the third MFTV assembly 98 prevents the matrix from being washed out of the separation capillaries 34. In a zone-electrophoresis application, as no gel matrix is employed, MFTV assembly 98 prevents the samples from being washed out of the separation capillaries 34. In both applications, however, an analyte to be detected must be charged as the migration is occurring without fluid flow.

In another embodiment, (not shown) the system analyzes a plurality of samples without employing a chromatographic column array 14. In this embodiment, the system contains a plurality of intake capillaries 3, each capillary having a reaction portion 8 that can optionally be housed in a heater assembly 9. The proximal portion 7 of each intake capillary 3 connects directly to cross-assembly 30 by junctions 32. Sample(s) are subsequently positioned at the injection region 91 of junctions 32 and the separation capillary array 33. Separation, either by electrophoresis or pressure flow, of the sample(s) yields at least one analyte in the sample(s) that is detectable by a detector 36 and includes a coherent light source 37. The distal portion 96 of each separation capillary 34 terminates in a buffer reservoir 35.

A wide variety of samples of biological, medical, ecological, or chemical interest can be analyzed without limitation. A "sample," as used herein, can include one or more analytes. Analytes of particular interest include macromolecules such as proteins, polypeptides, saccharides and polysaccharides; genetic materials such as nucleic acids and polynucleotides; carbohydrates; cellular materials such as bacteria, viruses, organelles, and cell fragments; metabolites; drugs; and the like; and combinations thereof. Proteins that are of interest include proteins that are present in blood plasma, such as albumin, globulin, fibrinogen, blood clotting factors, hormones, and the like. Other proteins that can be manipulated, separated and detected using the present system include interferons, enzymes, growth factors, and the like. Other chemicals that can be manipulated, separated and detected using the present invention include, but are not limited to, pharmaceuticals such as antibiotics, as well as agricultural chemicals such as insecticides and herbicides.

Of particular interest are samples containing macromolecules that are associated with the genetic materials of living organisms. Samples can be derived from blood and other tissues, organs or waste products. The analytes of interest include nucleic acids and oligonucleotides such as RNA, DNA, their fragments and combinations, chromosomes, genes, as well as fragments and combinations thereof. The invention is especially suited to applications involving DNA diagnostics, such as DNA template sequencing, DNA fragment analysis and DNA fingerprinting. Sequence variations as small as one base or base pair difference between a sample and a control can be detected. The detection and analysis of the above-mentioned analytes in a particular sample, is accomplished by employing the integrated multiplexed system of the invention.

Referring back to FIG. 1, the apparatus 1 of the invention is composed of multiple integrated components. A plurality of intake capillaries 3, each having a distal portion 6 and a proximal portion 7 relative to the T-assembly 12, are in fluid communication with delivery device 11 and the plurality of first junctions 13. The distal portion 6 of each intake capillary 3 further contains an inlet end 6a for the introduction of samples from the delivery device 11. The number of intake capillaries 3 employed in the system is directly related to the number of sample analysis "channels" in the system. The number of channels in the system, and thus the corresponding number of intake capillaries 3, is at least 2, preferably at least about 5, more preferably at least 8, even more preferably 96, and most preferably at least about 1000. The multiplexed system can conveniently be adapted to receive samples from a 96 well microtiter plate. Thus, once the number of channels desired in the system is established, the corresponding number of other components, i.e., intake capillaries 3, chromatographic columns 14 and separation capillaries 34.

The intake capillaries 3 pass through a plurality of first freeze thaw valves (MFTVs) 5. MFTVs 5, as with other MFTVs discussed herein, can be viewed as an "assembly" of individual freeze thaw valves that have been multiplexed. The size of this assembly will vary as the number of channels one selects to employ in the system varies. The MFTVs or a valve assembly permit the manipulation and control of fluid flow within apparatus 1.

In one embodiment, MFTVs 5 are positioned at both the distal portion 6 and the proximal portion 7 of each intake capillary 3. In this embodiment, MFTVs 5 contain two assemblies, e.g., a plurality of distal freeze thaw valves 5a and a plurality of proximal freeze thaw valves 5b that, as described in detail below, operates as a single freeze thaw valve assembly. Intake capillaries 3 are preferably made of fused-silica, however, other suitable materials, such as stainless steel or other metals can also be used. Optionally, each intake capillary 3 may also comprise a reaction portion 8. The reaction portion 8, permits mixing and reaction steps, such as dye-labeling terminator cycle-sequencing reactions, involved in nucleic acid analysis. Thus, each reaction portion 8 functions as a microreactor for the cycle-sequencing reactions. A microreactor array 2 is formed when the intake capillaries 3 are formed to have a reaction portion 8. The reaction portion 8 may be formed as a loop or other suitable structural conformation. Optionally, the reaction portion 8 can be positioned inside a heater assembly 9. The heater assembly 9 can be employed for analysis of samples that require heat processing, such as cycle-sequencing reactions for nucleic acid analysis. The intake capillaries 3 enter the heater assembly 9 by an aperture in the heater assembly. In a preferred embodiment, the heater assembly 9 is a hot air thermal cycler. The use of a reaction portion 8 positioned inside the thermal cycler permits greater volumes of sample to be heated. A suitable thermal cycler is available from Idaho Technology, Idaho Falls, Id.

Thus, if required, heat can be applied to one or more intake capillaries 3 to facilitate or initiate a reaction to yield a plurality of reacted samples. Application of the heater assembly 9 is useful when the samples are nucleic acids, such as RNA or DNA.

Figure 5:
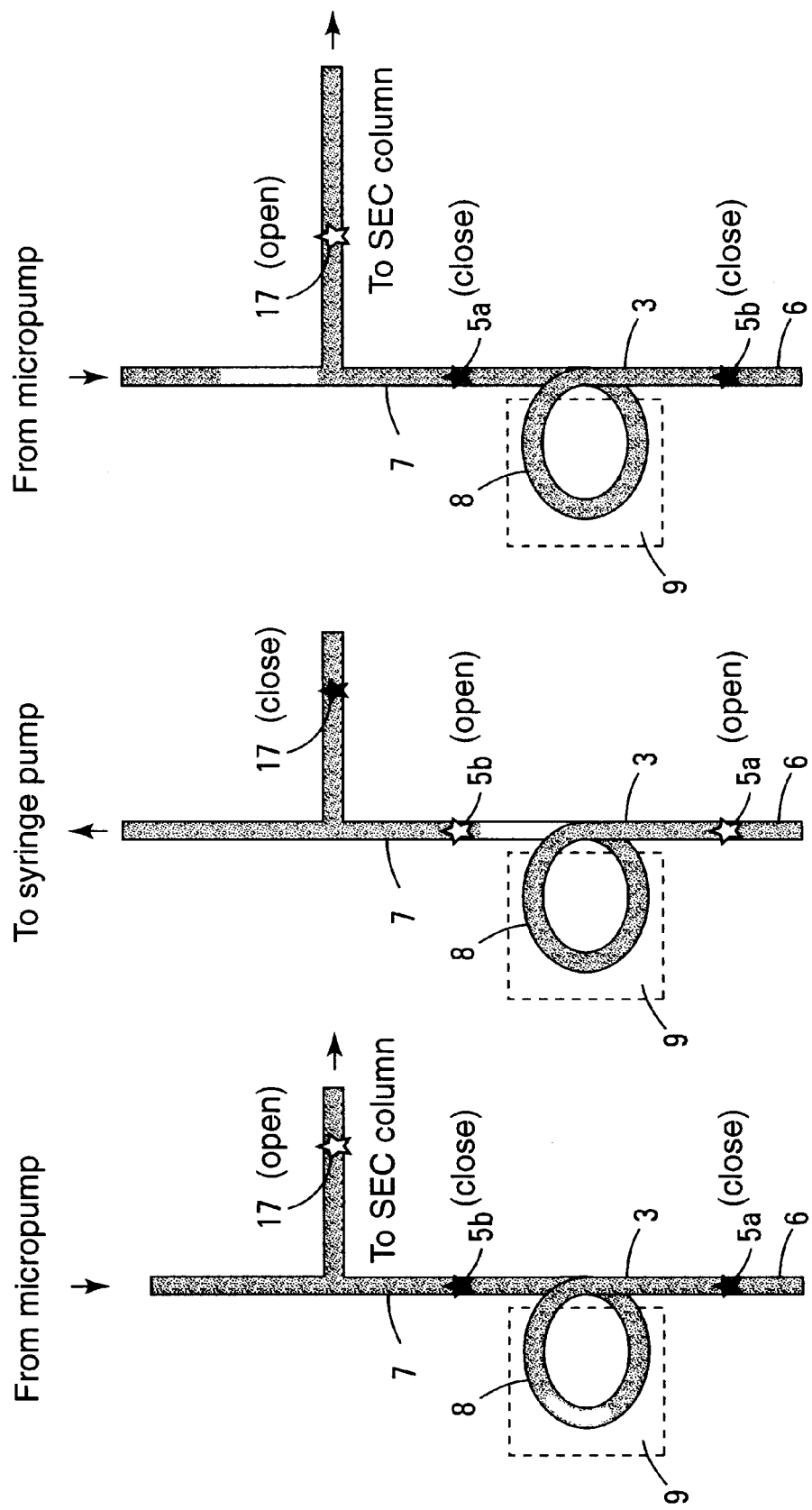
FIG. 5A shows system operation wherein MFTV 17 is open and MFTVs 5 are closed.
FIG. 5B shows system operation wherein MFTV 17 is closed and MFTVs 5 are open.
FIG. 5C shows system operation wherein MFTVs 5 are closed and MFTV 17 is open.

Referring now to FIGS. 5A–5C, the optional reaction portion 8 of individual reaction capillaries 3 are positioned inside the heater assembly 9. Preferably, there is about 20 centimeters (cm) to about 80 cm of each reaction portion 8 residing inside the heater assembly. More preferably, there is about 30 cm to about 50 cm of each reaction portion 8 residing inside the heater assembly 9. As shown, the distal portion 6 and the proximal portion 7 of each individual intake capillary 3 are in fluid communication with and pass through MFTVs 5. MFTVs 5a, positioned at distal portion 6 of each intake capillary, and MFTVs 5b, positioned at the proximal portion 7 of each intake capillary 3, act in unison. Thus, fluid flow is controlled in each intake capillary 3 by a cooled or super-cooled liquid that is controlled by cryogenic solenoid valves (not shown). Cooling at a specific MFTV assembly creates a solid "plug" of fluid that stops fluid flow at that MFTV location. This process is described in more detail below. A "cooled" or "super-cooled liquid," as used herein, refers to a liquid that is sufficient to create a solid plug of fluid in a MFTV assembly. Thus, depending on the fluid, buffers employed in a system and the samples to be analyzed, the cooled or super-cooled liquid may vary. Typically, the cooled liquid is liquid nitrogen or an equivalent thereof.

Figure 2:
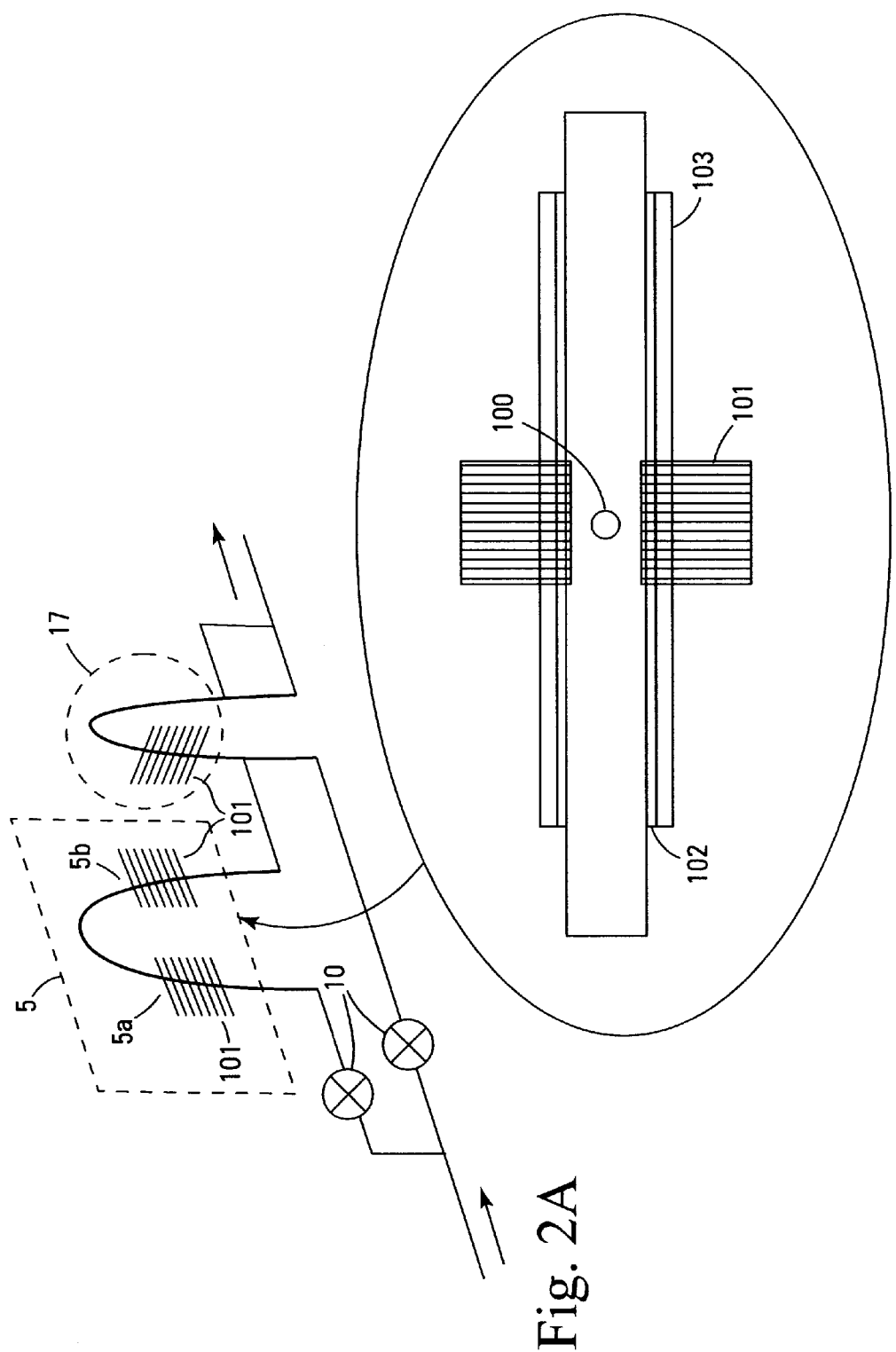
FIG. 2A is a schematic of multiplexed freeze/thaw valve assemblies (MFTV) 5 and 17 employed in a system of the invention.
FIG. 2B is a schematic of a single MFTV assembly.

Referring now to FIG. 2A, a schematic of MFTV assemblies 5 and 17 are shown. MFTV assemblies 5 and 17 are controlled by cryogenic solenoid valves 10 which are employed to control the flow of a cooled or super cooled liquid in the assemblies. Suitable solenoid valves 10 are available from, for example, Valcor Scientific, Springfield, N.J. As shown in FIG. 2B, each MFTV assembly 5 and 17 utilized in the invention contains a tubing array 101, a centrally located thermocouple 100, positioned so as not to have direct contact with the tubing array 101, and a heater 102. Preferably, thermocouple 100 is a small K type thermocouple available from Omega, Stamford, Conn., and the tubing array 101 is a metal material or portion, e.g., a hypodermic metal tubing, or other suitable type of tubing that can support cooled or super cooled liquid flow and is preferably heat conductive.

Optionally, a heat insulator 103, made of a suitable insulating material, can be placed externally to the heater and tubing array to prevent energy loss. The thermocouples 100 installed in MFTV assemblies 5 and 17 detect changes in temperature and permit control of solenoid valves 10. Preferably, a MFTV assembly contains a plurality of capillaries and a plurality of heat conductive portions. Typically, at least a portion of each capillary contains a fluid and the valve assembly is closed by contacting the heat conductive portions with a cooled or super cooled liquid. Thus, contact of the cooled or super cooled liquid to the heat conductive portions is effective to solidify the fluid in the capillaries.

Referring now to FIG. 2B, MFTV assemblies 5 and 17 can be closed by lowering the temperature in the tubing array 101 to an appropriate temperature to allow "plug" formation within a capillary by opening cryogenic solenoid valves 10. Opening of these valves allows a cooled or super cooled liquid, such as liquid nitrogen, to flow into the tubing array 101. To open MFTV assembly 5 and 17, the temperature of the heater 102 is increased so that the "plug" inside each capillary thaws and is a flowing fluid. MFTVs 5a, positioned at the distal portion 6 of each intake capillary 3, and MFTVs 5b, positioned at the proximal portion 7 of each intake capillary 3, are synchronized, so that the temperature monitored at each valve assembly is used for feedback to indicate whether further heating or cooling is required. Each valve of the MFTVs 5 contain a portion of an intake capillary 3 and are positioned at the distal portion 6 and the proximal portion 7 of each intake capillary 3. The proximal and distal valves of MFTVs 5 can be considered as essentially one multiplexed on/off valve. MFTVs 17, however, operate independently of MFTVs 5.

Previous attempts to integrate sample processing technologies with analyte separation technologies involved the use of multiple rotary valves used to control system flow (Tan et al., Anal. Chem. 69:664–674 (1997)). The rotary valves proved to be excessively bulky and required a large number of parallel valves that would eventually limit scaling up of the integrated-multiplexed online system. As disclosed herein, the strategy to solve this complex problem is to design a distribution network that reduces the number of parallel valves and replaces rotary valves with multiplexed freeze thaw valve (MFTV) assemblies. By employing MFTV assemblies, the on/off operations of the system, as described above, can be accomplished according to a freeze/thaw principle described in Bevan et al., Chromatogr. A., 697:541–548 (1995), and Bevan et al., Anal. Chem. 67:1470–1473 (1995)). The advantages of MFTV assemblies include, for example, non-invasive operation which reduces the risk of sample contamination, zero dead volume, rapid response time, low cost, high pressure tolerance, elimination of mechanical motion and good electrical isolation.

The system described by Bevan et al., in the publications above, employs carbon dioxide ($CO_2$). A $CO_2$ system is not amenable to multiplexing and multiple mechanical limitations arise when utilizing more than 3 to 4 channels. This is so because $CO_2$ cooling is based on gas expansion and has the capacity to affect only very small localized areas. Thus, to regulate the flow of a liquid within a tube or tubing, a fine spray must be directed onto the outer surface of each tube. This must be performed at each position on the tube where freezing is desired. Additionally, only narrow tubing can be utilized in $CO_2$ cooling as the fluid volume in the tubing directly affects the speed with which a channel can be opened or closed. These requirements described above would render any system scale-up, as described herein, excessively bulky and very impractical. For example, in one embodiment, the apparatus of the present invention can utilize 96 channels and employ MFTVs at four different points for each channel. In contrast, as described below, multiplexing a system by a series of freeze thaw valves is very amenable to scale-up.

The response time for an MFTV assembly depends on the design and thermal conductivity of the materials used to construct each valve. The design described herein not only prevents the fragile capillaries from being broken once frozen but also sends the waste gas out of the instrument. The MFTV on/off switching mechanism demonstrated herein is readily scalable from 2 to 1000 or more channels without any modifications or negative effects on performance. For 96 channels, one only has to employ, for example, rectangular tubing comprising sufficient inner dimensions (e.g., 3.6 centimeters (cm) wide by 370 (micrometers ($\mu$m)) to replace the tubing array 101 as shown in FIGS. 2A and 2B. With better thermal contact and higher cooled or super cooled liquid flow, 1000 or more valves operated in parallel should also be manageable in a relatively confined space.

Referring now back to FIG. 1, the proximal portion 7 of each intake capillary 3 passes through MFTVs 5 and connects to T-assembly 12. T-assembly 12, by means of junctions 13, further connects to first manifold 15. Junctions 13 in the T-assembly 12 function to connect each proximal portion 7 of each intake capillary 3 through MFTV 17 by means of the first joining capillaries 27. Each of the first joining capillaries 27 subsequently connect to a corresponding chromatographic column 14a in the chromatographic column array 14. First manifold 15 further connects to valve system 16. Valve system 16 is connected to a pump 18 and a syringe pump 19. In a preferred embodiment, these elements are controlled by computer 20.

Figure 3:
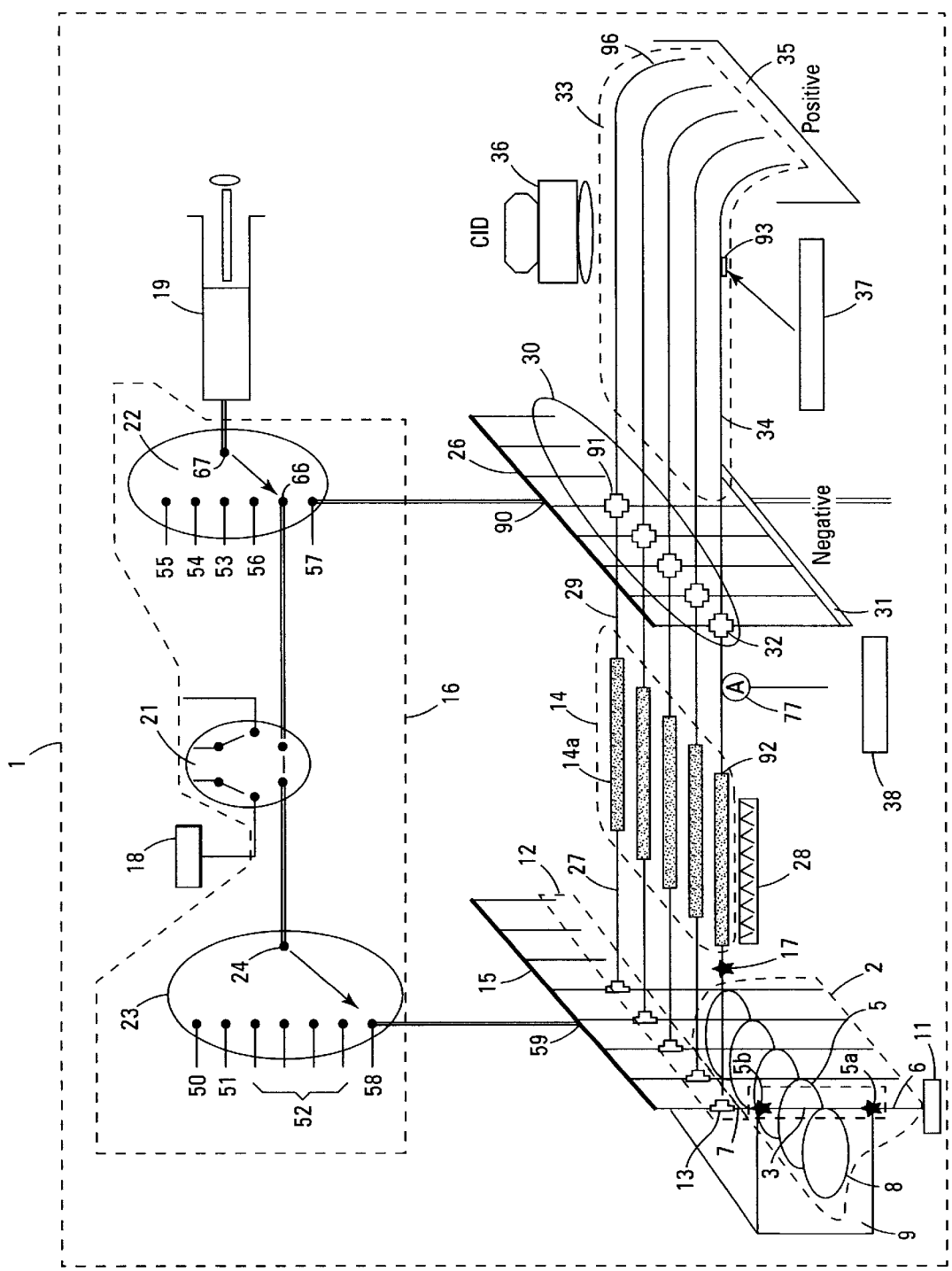
FIG. 3 is a schematic of one embodiment of the integrated multiplexed system design comprising eight channels.

Referring now to FIG. 3 for additional detail, T-assembly 12 has a plurality of individual first junctions 13. As described above, junctions 13 in the T-assembly 12 permit connections to be made between the first manifold 15, the proximal portion 7 of each intake capillary 3, and a corresponding first joining capillary 27. Each of the first joining capillaries 27 subsequently connect to a corresponding chromatographic column 14a in the chromatographic column array 14. Preferably, junctions 13 are a set of conventional HPLC T-shaped joints available from, for example, Valco Instruments, Houston, Tex. This arrangement is utilized for each individual intake capillary 3 and helps to ensure a subsequent quantitative injection into the chromatographic column array 14.

In one embodiment and as further shown in FIG. 3, valve system 16 can contain three different valves which include a motorized 2-position injection valve 21, a 6-position motorized valve 22, and an 8-positioned motorized valve 23 having a center port 24. As discussed below, the connections made between the valves, reagents, buffers, and other system components are through tubing made of a suitable material such as stainless steel or other metal, rubber, polyurethane, or TEFLON. Valves 21, 22, and 23 are individually available, for example, from Valco Instruments, Inc., Houston, Tex. Valve 21 connects to a center port 24 of valve 23. Additional positions of valve 23 are connected to a waste line 50, a manual syringe 51 and regeneration reagent reservoirs 52. Port 58 of valve 23 connects to the center port 59 of the first manifold 15.

Figure 4:
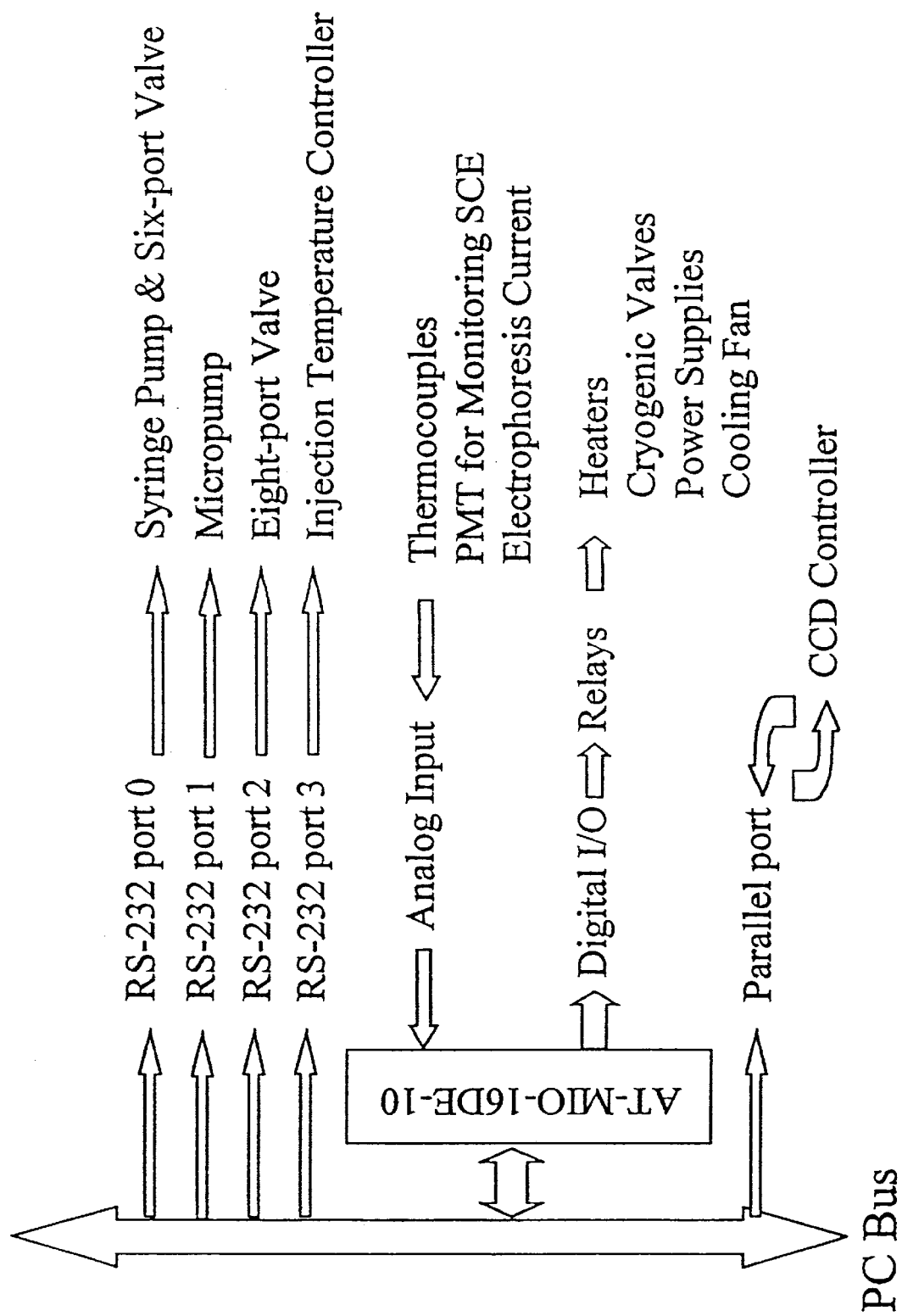
FIG. 4 shows a computer control protocol for the integrated multiplexed system in FIG. 3.

A first position of valve 21 connects to pump 18, available from, for example, Ultra-plus MicroLC System, Micro-Tech Scientific, Sunnyvale, Calif. A second position of valve 21 connects to a port 66 of valve 22. A port 67 of valve 22 connects to syringe pump 19. Preferably, the syringe pump 19 is fitted with a 0.5 milliliter (mL) to a 20 mL syringe, and more preferably a 1 mL to a 2 mL syringe, available from Kloehm Company, Inc., Las Vegas, Nev. The remaining ports of valve 22 are connected to reservoirs of a suitable running buffer 53, water 54, preferably deionized or distilled water, an albumin solution 55, preferably bovine serum albumin (BSA) or human serum albumin (HSA), and a waste container 56. Port 57 connects to a center port 90 of a second manifold 26. The valves and pumps employed herein can be activated by an electronic signal received from computer 20. Two serial ports of the computer 20 and two additional ports of an AT-232/2 board provide four communication channels which are employed to control the syringe pump 19, valve 22, pump 18, and valve 23 (FIG. 4).

Referring now back to FIG. 1, each of the first joining capillaries 27 pass through MFTV assembly 17, and provide fluid communication to the individual chromatographic columns 14a in the chromatographic column array 14. Depending on the samples to be analyzed, chromatographic columns 14a of the chromatographic array 14 can be, for example, columns suitable for size-exclusion purification (SEC), ion-exchange, reverse-phase, hydrophobic columns, normal phase, and affinity purification. However, the invention is not limited to any particular type of column chromatography or sample processing technology. In a preferred embodiment, the chromatographic columns are SEC columns. Optionally, a water bath 28 is employed if heating of the columns is desired. The columns can be heated to a temperature of about 40° C. to about 80° C. Preferably, the columns are heated to about 60° C.

Each of the second plurality of joining capillaries 29 are connected to a chromatographic column 14a by outlet end 92 of the second joining capillary 29, and to the cross-assembly 30 by junctions 32. Junctions 32 operate as multifunctional devices for denaturation, pre-concentration, and sample injection. These operations are described more fully below. Junctions 32 connect to the second manifold 26 and the third manifold 31 by at least one source of tubing made of a suitable material such as stainless steel or other metal, rubber, polyurethane, or TEFLON or a combination thereof Junctions 32 further connect directly to an individual separation capillary 34 in the separation capillary array 33. Sample elution from at least one chromatographic column 14a to the plurality of second junctions 32 is monitored by detector 38. Detector 38 is capable of transmitting a signal to computer 20 by means of a lens 39, an objective 40, and photomultiplier tube 41.

In a preferred embodiment, lens 39 is an uncoated plano-convex lens, and objective 40 is a 5× to a 50×microscope objective. The lens 39 that is employed should have a suitable focal length that can be used to focus the laser 38 on the capillary window 77 of at least one of the second joining capillaries 29. Useful lenses, such as a 12 millimeter (mm) lens, are available from Edmund Scientific, Barrington, N.J. The microscope objective 40, is available from, for example, Edmund, and can also be used to focus and collect emitting fluorescence perpendicular to the excitation laser. Optionally, a cutoff filter can be employed to block scattered light and is dependant upon the excitation laser employed. Thus, if a 514 nm laser is utilized, a cutoff filter suitable for 514 nm is used. In a preferred embodiment, the cutoff filter is a RG610 filter available from, for example, Corning Glass, Corning N.Y. A wide variety of photo-multiplier tubes 41 can be employed. In one embodiment, an R928, available from Hamamatsu Corp., Bridgewater, N.J., operating at 1000 V, can be used to generate an electrical signal to computer 20. The signal can be digitized at analog input channel of a multifunctional data acquisition board, e.g., AT-MIO-16DE-10, available from National Instruments, Austin, Tex.

Referring back now to FIG. 3, and as described above, cross assembly 30 contains a plurality of individual second junctions 32. In a preferred embodiment, the junctions 32 are PEEK crosses, available, for example, from Upchurch Scientific. The number of junctions 32 employed in the system is dependent upon the number of individual second joining capillaries 29 connected to a corresponding chromatographic column 14a in the chromatographic column array 14. Clearly, this number will further correspond to the number of separation capillaries 34 connected to junctions 32 of the cross assembly 30. Optionally, a fan can blow air into the entire cross assembly 30 for cooling junctions 32. Additionally, a suitable temperature monitoring system can be employed, such as, a heating tape and a thermocouple. Suitable heating tapes and thermocouples that can be employed in the system are available from Omega, Stamford, Conn.

Each of the plurality of individual second junctions 32 in the cross assembly 30 perform several functions in the system. First, junctions 32 interface chromatographic column array 14 with the separation capillary array 33 to allow sample injection. One type of injection is the "heart-cut" injection. A heart cut injection is an injection that is synchronized with the system current (in microamps) at the rising and falling portion of a signal derived from laser-induced fluorescence. (See, for example, FIGS. 7A and 7B). Second, if a heating tape is employed around junctions 32, it can raise the temperature of the samples being analyzed to facilitate sample denaturation while injecting (commonly known as a "hot" injection). Third, junctions 32 supply separate buffer flows to the individual separation capillaries 34 in the separation capillary array 33, and collect waste from the individual chromatographic columns 14a and the transverse flows from syringe pump 19 by way of second manifold 26 and third manifold 31. Connections between the second manifold 26 and the third manifold 31, as described above, should be made as symmetrical as possible to provide uniform and near equivalent flow rates at each separation capillary 34 in the separation capillary array 33 during a given run. Finally, junctions 32 maintain electrical contact for each separation capillary 34 for an electrokinetic injection into the separation capillary array 33 at the injection region 91.

As shown in FIG. 3, the separation capillary array 33 as utilized herein is described in U.S. Pat. No. 5,582,705. Briefly, in capillary electrophoresis, a buffer-filled capillary is suspended between two reservoirs filled with buffer and an electric field is applied across the two ends, an inlet and outlet end, of the capillary. In the present invention, the proximal portion 97 of each separation capillary 34 is in fluid communication with a corresponding second joining capillary 29 by junction 32.

Referring back to FIG. 1, in the present invention the inlet end 97a of each separation capillary 34 receives a chromatographed sample directly from each second joining capillary 29 through a junction 32. Samples are then injected at the injection region 91 of each individual separation capillary 34 and migrate through the distal portion 96 outlet end 96a of separation capillary 34 that provides a low potential end and reservoir 35. to allow separation of individual sample components. During this migration, analytes contained within the samples are preferably electrophoretically separated, however, other methods known in the art, such as separation by pressure flow, can also be employed.

Analytes are preferably detected by second detector 36, and detection is effected while the samples are still in the separation capillaries 34 by a coherent light source 37. Side-entry irradiation of analytes in the separation capillaries 34 of the separation capillary array 33 is effected through the transparent window portion 93 of each separation capillary 34 in the separation capillary array 33, as shown in FIG. 3. Light passes through the transparent window portion 93 of each capillary 34 in a sequential manner. The coherent light source 37 is positioned to direct a bean of coherent light along a transparent path. The coherent light source produces light waves traveling together in phase. The light preferably has a wavelength of about 200 nanometers (nm) to about 1,500 nm. Preferably, the coherent light source is a laser. An argon laser operating simultaneously at one or more visible lines is typically used for excitation, although other light sources and wavelengths can also be used. Particularly preferred excitation wavelengths are 488 nm and 514 nm. Preferably, light source 37 is a 514 nm $Ar^+$ laser. A pure output laser, i.e., a laser emitting light of a single wavelength, is a particularly preferred light source. Alternatively, the wavelength of the laser can be chosen by an interference filter or a glass prism. Side entry irradiation as utilized herein is described in, for example, U.S. Pat. Nos. 5,582,705, 5,741,411 and 5,695,626.

As shown in FIG. 3, second detector 36 preferably includes a two-dimensional image array detector, especially in the system described herein, although first and second linear detectors may also be employed, one for each channel. More preferably, a charge-coupled device (CCD) or a charge-injection device (CID) is used. In the system described herein, where detection is effected using a CCD, optional rectangular filters with dimensions in excess of the separation array 33 dimensions may be conveniently used to split fluorescence emissions simultaneously induced from analytes in the individual separation capillaries 34 of the separation capillary array 33.

Operation of the integrated multiplexed apparatus 1, as described above, typically involves introducing a sample or plurality of samples into the chromatographic column array 14 followed by chromatographic separation to yield a purified sample(s), and separating and detecting an analyte in the purified sample. A typical method employing the system described above is discussed below.

The invention provides a multiplexed method for processing and detecting an analyte concurrently in a sample or a plurality of samples. A variety of samples, described above, can be analyzed employing the system described herein. Significantly, a variety of "differing" samples can be analyzed simultaneously as, described above, each channel is unique. However, a plurality of samples need not be different but may include multiple runs of a single sample. The invention is preferably suited for use in DNA analysis and sequencing of DNA sample templates, and DNA diagnostics experiments where the targeted analytes are DNA fragments and all four nucleotide bases are detected.

Referring now to FIG. 3, turning on pump 18, opening MFTVs 5a and MFTVs 5b, and closing MFTVs 17, a sample containing analytes of interest, is preferably introduced into the inlet end 6a of distal portion 6 of an individual reaction capillary 3. Sample introduction is typically from a suitable sample delivery device 11 that is capable of containing a sample aliquot. As shown in FIGS. 5A–5C, and as described above, the plurality of first MFTVs 5 includes NMFTVs 5a and MFTVs 5b. MFTVs 5a, contain a portion of each distal portion 6 of intake capillary 3, and MFTVs 5b contain a portion of proximal portion 7 of intake capillary 3. Typically, sample aliquots can range between about 5 nanoliters (nl) to about 1 (milliliter) mL. Preferably, the delivery device is a microtiter plate.

FIGS. 5A–5C further show a typical automated process that introduces a sample or plurality of samples from delivery device 11 (not shown), to an individual intake capillary 3 having an optional reaction portion 8. In FIG. 5A, the sample 70, shown in white, is positioned inside reaction portion 8, where heating of the sample, if desired, can be initiated. MFTVs 5a and 5b are closed and MFTVs 17 are open. FIG. 5B shows sample 70 exiting reaction portion 8 by activation of syringe pump 19 (not shown). Sample 70 is removed by opening MFTVs 5a and 5b and closing MFTVs 17. FIG. 5C shows sample 70 positioned in a small region of the first manifold 15 (not shown). By subsequent closing of MFTVs 5a and MFTVs 5b and opening MFTVs 17, sample 70 is delivered to a purification column 14a in the purification column array 14 (not shown). Pump 18 (not shown) typically remains turned on during this process.

In a preferred embodiment, nucleic acid containing samples are analyzed and the reaction portion 8 is housed in heater assembly 9 which is typically a hot-air thermal cycler. A plug of deionized water is typically also loaded into the intake capillary 3 to ensure the sample reaction mixture is properly positioned in the reaction portion 8 of the intake capillary 3 inside the heater assembly 9 as shown in FIG. 5A. As described below in the detailed examples, depending on the length and diameter of an individual intake capillary 3 and reaction portion 8, the plug of deionized water assists to properly position an adequate volume of sample, for example, in the reaction portion 8. Thus, once an adequate sample volume is positioned inside the reaction portion 8, MFTVs 17 are opened and MFTVs 5 are closed and heat catalyzed cycle-sequencing reactions are initiated. During this reaction time, a suitable buffer continuously flushes the chromatographic columns 14a in the chromatographic column array 14 at a preselected flow rate, for example, about 100 microliters ($\mu$l) to about 800 $\mu$l. Suitable buffers include various salt solutions and Tris-EDTA (TE) buffer. In a preferred embodiment, each chromatographic column 14a in the chromatographic column array 14 are size-exclusion columns (SEC).

With reference to FIG. 5B, after completion of a reaction, MFTVs 17 are closed and MFTVs 5 are opened so that the reaction samples or mixtures are aspirated, by pump 19 (not shown), through junctions 13 (not shown), of the T-assembly 12 (not shown) and positioned into the tubing above the first manifold 15. Pump 18 is turned off during this process. Once the reacted samples are positioned in the tubing above the first manifold 15 (not shown), MFTVs 5 are closed and MFTVs 17 are opened (FIG. 5C). Buffer flow is reversed, by selecting valve 21 and re-activating pump 18. Turning on pump 18 permits the transferring of the reacted sample or plurality of reacted samples from each of the intake capillaries 3 into the chromatographic columns 14a of the chromatographic column array 14.

As described above a variety of chromatographic columns can be employed in the invention. Thus, using pre-selected chromatographic columns 14a for purification, a plurality of purified sample portions can be obtained that comprise at least one detectable analyte. An analyte can be detected, for example, by an image array detector in concert with a coherent light source. In a preferred embodiment, the analytes are DNA Sanger reaction fragments which are products of cycle-sequencing reactions.

Once purified sample portions are obtained, the sample portions can be injected at each of the injection regions 91 into a corresponding separation capillary 34 in the separation capillary array 33. Before this injection, however, several steps are taken. First, pump 18 is turned off, pump 19 is turned on and the each chromatographic column 14a in the chromatographic column array is washed. Second, prior to injection into the separation capillary array 33, the temperature to perform the injection at the cross assembly 30 should be determined. Junctions 32 of the cross assembly 30 can optionally be pre-heated by means of a suitable heating tape to a temperature of between about 50° Celsius (C.) to about 100° C. Preferably, junctions 32 are heated to about 65° C. to about 90° C. Finally, typically prior to sample injection, water or other appropriate buffers from the ports of valve 22, are selected to flow through the injection region 91 by activating syringe pump 19. In a preferred embodiment, deionized water is employed. The flow rate of the deionized water or other buffer flowing through the injection region 91 is typically about 50 $\mu$l to about 700 $\mu$l. Preferably, the deionized water or buffer flow rate is about 100 $\mu$l to about 300 $\mu$l. In a preferred embodiment, the continuous transverse flow of deionized water at the proximal portion 97 of the plurality of separation capillaries 34, is sufficient to cause dialysis at the interface of a sieving matrix in the separation capillaries and creates a low ionic strength zone. This further promotes stacking injection for pre-concentration of the samples. When the steps described above have been satisfied and while washing of the chromatographic columns 14a is occurring, pump 18 is again turned on, pump 19 is turned off, an injection is made, e.g., heart-cut injection, and samples migrate through the separation capillaries 34 towards the distal portion 96 of the separation capillaries 34 which provides a low potential end to reservoir 35. This is described more fully below.

When the purified sample portions reach the first detector 85 positioned at point A 77 (FIG. 1) of the second joining capillaries 29 (as recognized by the onset of a peak, see FIG. 7), an electrokinetic injection to each separation capillary 34 of the separation capillary array 33 is performed. When the injection of the purified sample portions is completed (at about one-third of the peak height on its falling edge) MFTVs 17 are closed, syringe pump 19 is turned on and valve 21 selects syringe pump 19. A suitable buffer is used to remove the deionized water and re-ionize the injection zone at a very low flow rate to avoid losing any of the injected purified sample portions. Suitable buffers include a variety of buffers useful in electrophoresis. Preferably, the buffer employed is about 0.5×Tris-borate/EDTA (TBE) buffer to about 5.0×TBE buffer. The buffer transverse flow is pre-programmed to about 100 microliters ($\mu$L)/minute/capillary to about 800 $\mu$L/minute/capillary, and during electrophoretic separation set at about 50 volts/centimeter (V/cm) to about 300 V/cm.

If one or more of the individual junctions 32 of the cross assembly 30 are heated or pre-heated, e.g., for samples such as nucleic acids to be analyzed, the temperature at the injection region 91 of the cross assembly 30 typically is lowered to a suitable temperature, e.g., room temperature, as quickly as possible after heating to restore the ionic strength at each of the junctions 32. Concurrently, MFTVs 17 can be opened and regeneration of the purification columns 14a and reaction portions 8 of each intake capillary 3 can proceed after the electrophoresis current has stabilized. This process typically takes between 30 and 50 minutes. The sieving polymer matrix employed in the separation capillaries of the invention is generally of a sufficiently low viscosity so as to enable it to be pushed into the separation capillaries by pressure. The polymer matrix preferably has a viscosity of less than about 5,000 centipoise, more preferably less than about 2,000 centipoise, measured in a capillary at 1 atmosphere (atm), 25° C., using the Pouiselle equation.

In one embodiment of the invention, the matrix is preferably a single polymer matrix prepared from PEO with $M_n$ of between 2,000,000 and 9,000,000 at a concentration of about 1% to about 5%. However, other polymer matrixes can be employed such as polyvinylpyrrolidone (Gao et al., *Anal. Chem.* 70:1382–1388 (1998)) (PVP, 4.5% with 27 centipoise (cp), polydimethylacrylamide (Madabhushi et al., *Electrophoresis* 19:224–230 (1998)) (PDMA, 6% with 75 cp) and polyacrylamide. In another embodiment, a polymer matrix is absent and sample analysis can occur by zone-electrophoresis. Note that if a zone-electrophoresis method is utilized, as described above, the optional third plurality of MFTVs 98 should be employed to stop fluid flow within separation capillaries 34. MFTVs 98 would typically operate in a manner previously described above for MFTVs 5 and MFTVs 17.

Any convenient detection method may be used to detect each of the detectable analytes separated in a capillary electrophoresis system utilizing the polymer matrix of the invention. Fluorescence detection and detection using a mass spectrometer are preferred. However, electrochemical detection utilizing a small electrode positioned at the outlet end 96a of the distal portion 96 of the separation capillaries 34 can also be used.

The intake capillaries 3 having the reaction portion 8 (making up the microreactor array 2 as shown in FIG. 1, the cross assembly 30, and the T-assembly 12 are typically regenerated by flushing with a salt solution, a suitable buffer, methanol, and deionized water sequentially. Preferably, the salt solution is NaOH and is between about 0.05 molar (M) and about 1 M NaOH, and the buffer is a TE buffer. Each of the chromatographic columns 14a can also be regenerated by a salt solution and suitable buffer if desired. The syringe pump 19 is preferably rinsed with deionized water and the loading reagent whenever it exchanges reagents. All the regeneration steps described herein are typically automated by control of the syringe pump 19 except that the regeneration of the separation capillary array 33 can be performed manually with a suitable syringe.

Achieving uniform or equivalent flow rates in the intake capillaries 3 and, if utilized, the reaction portions 8, the separation capillary array 33 and the chromatographic column array 14, is an important aspect of system operation. The accuracy of sample loading, the timing of the injection at the cross assembly 30 and into the chromatographic column array 14, will depend primarily upon how uniform the flow rates are among each individual channel. To ensure flow uniformity, Pouiselle's law is typically observed. According to Pouiselle's law, the flow rate in a tube is primarily dependent on the pressure drop in the tube, the length of the tube, the average inner diameter of the tube, and the temperature and viscosity of the fluids inside the tube. The internal diameter of the capillary, the pressure drop, temperature and viscosity among the channels are essentially identical. The capillary length can be adjusted to achieve a uniform and controllable flow rate.

In a preferred embodiment, the system of the invention, analyzes DNA samples to their primary sequences. The system automatically processes these samples through reaction, purification, denaturation, pre-concentration, injection, separation and detection in a parallel fashion. The dye-labeled terminator cycle-sequencing reactions are performed in the reaction portion 8 of the intake capillaries 3 positioned in the heater assembly 9. Subsequently, the DNA samples are directly loaded into separate SEC columns for purification. The on-line denaturation and stacking injection for capillary electrophoresis is typically simultaneously accomplished at the injection region 91 at the cross assembly 30 and separation capillary array 33 interface. The separation capillary array 33, the reactive portion 8 of the intake capillaries 3, and purification columns 14 are all typically regenerated after each run, by the computer controlled pump 18 and syringe pump 19 and valves 16, as shown in FIG. 1. In this preferred embodiment, as shown in Example 3, the data demonstrates base calling up to 460 base pairs (bp) with accuracy of about 98%.

The invention will be further described by reference to the following detailed examples which are exemplary and not intended to limit the invention.

EXAMPLE 1

Preparation of Reagents and Buffers

A 1×Tris-borate/EDTA (TBE) buffer solution was prepared by dissolving a pre-mix (Amerosco, Solon, Ohio) of 89 (millimolar) mM tris(hydroxymethyl)aminomethane (THAM), 89 mM boric acid, and 2 mM ethylenediaminetetraacetic acid (EDTA) with 3.5 M urea in deionized water (pH ~8.3). A 1×Tris-EDTA (TE) buffer solution was prepared by dissolving 10 mM tris(hydroxymethyl) aminomethane (THAM) and 2 mM ethylenediaminetetraacetic acid (EDTA) in deionized water, adjusted to a pH of about 9.0 by 1.0 M HCl. Bovine serum albumin (BSA) and deionized formamide were from Sigma Chemical (St. Louis, Mo.).

Fresh 5 mg/mL BSA solution was prepared daily by adding 100 mg bovine serum albumin to 20 mL deionized water, stirring in an ultrasonic bath for 5 min, and degassing in a vacuum chamber. Methanol, anhydrous sodium hydroxide and fuming hydrochloric acid were obtained from Fisher (Fairlawn, N.J.). Urea was purchased from ICN Biomedicals (Aurora, Ohio).

Poly(ethylene oxide) (PEO) was purchased from Aldrich Chemical (Milwaukee, Wis.). The sieving matrix was made by dissolving 1.5% of 8,000,000 MW PEO and 1.4% of 600,000 MW PEO in 1×TBE buffer. The two kinds of PEO powders were first mixed well and slowly pulled into 1×TBE buffer while being stirred violently. The violent stirring motion was maintained for two hours, and then replaced by a slow stirring motion until all noticeable bubbles were removed and a uniform and substantially clear gel was formed (approximately 8 hours). Two percent of 1,000,000 MW polyvinylpyrrolidone (PVP) from Polyscience (Warrinton, Pa.) in 1×TBE buffer was used to coat the separation capillaries between runs.

EXAMPLE 2

Instrument Operation and Sample Preparation for DNA Sequencing

Eight pieces of 77 cm long, 250 $\mu$m inner diameter (i.d.) and 360 $\mu$m outer diameter (o.d.) fused silica intake capillaries 3 were positioned through MFTVs 5a and MFTVs 5b. The intake capillaries 3 were formed to have reaction portions 8 (making a microreactor array 2) and were connected to the T-assembly 12 by first joining junctions 13. Each reaction portion 8 was positioned inside a hot-air thermal cycler 9 (Idaho Technology, Idaho Falls, Id.), through a small hole drilled on the side of the hot-air thermal cycler (FIG. 3). The T-assembly 12 employed a set of conventional HPLC T-shaped joints (Valco Instruments, Houston, Tex.) assembled on a metal rod. The distance from the T-assembly 12 to the proximal MFTVs 5 was about 8 cm (approximately 4 $\mu$L for each capillary) and the distance from the distal portion 6 of each intake capillary 3 to the distal MFTVs 5 was about 15 cm (approximately 7.5 $\mu$L). The distance between the proximal and distal valves of MFTVs 5 and the hole in the thermal cycler, was about 7 cm (approximately 7 $\mu$L). Thus, there was about 40 cm (approximately 20 $\mu$L) of each reaction portion 8 of each intake capillary 3 sitting inside the thermal cycler 9.

Fifteen cm lengths of 0.02 inch inner diameter (i.d.), 1/16 inch outer diameter (o.d.) TEFLON tubing (approximately 30 $\mu$L) for each of the eight channels were used to connect the T-assembly 12 with first manifold 15 (Valco Instruments). At the distal potion 6 of the intake capillaries 3 of the microreactor array 2, a holder was utilized to separate the intake capillaries to form a line and to align the tip of each intake capillary 3 with the center of a row of a 96-well microtiter plate 11. Reaction mixtures were then directly loaded into the intake capillaries of the microreactor array from the microtiter plate (see, for example, FIGS. 1 and 3).

DNA polymerase (Thermo Sequenase, Amersham Life Science, Cleveland, Ohio) and rhodamine dideoxy dye-terminator kit (Applied Biosystems, Foster City, Calif.) were used to preformed dye-terminator cycle sequencing reactions in the intake capillaries of the microreactor array. A typical 20 μL reaction mixture in each channel was composed of 2 μL of 2.0 mg/mL BSA, 4 μL of ddNTP mixture (0.22 micromolar (μM) ddATP, 2.0 μM ddCTP, 0.1 μM ddGTP, and 2.75 μM ddTTP), 2 μL of dNTP mixture (3.0 mM dATP, 3.0 mM dCTP and 3.0 mM TTP), 3.6 μL of 5.0 mM dITP (Sigma Chemicals, St. Louis, Mo.), 1.6 μL of reaction buffer (260 mM Tris-HCl and 65 mM $MgCl_2$ at pH approximately 9.5), 2 μL Thermo Sequenase dilution buffer (10 mM Tris-HCl, pH 8.0, 1 mM 2-mercaptoethanol, 0.5% Tween-20, 0.5% Nonidet P-40), 0.5 μL of Thermo Sequenase storage buffer (32 U/μL Thermo Sequenase, 20 mM Tris-HCl, pH 8.5, 50% glycerol, 0.1 mM dithiothreitol, 100 mM KCl), 1 μL of 5.0 μM -40M13 universal primer, 1.7 μL of 0.2 μg/μL M13mp 18 ss-DNA in 1×TE buffer (pH was approximately 7.5, Amersham), and 1.6 μL of deionized water. The temperature protocol was performed as described in Tan et al., Anal. Chem., 69:664–674 (1997). Reaction mixtures were heated to 96° C and held for 2 minutes; 30 thermal cycles were performed with denaturation at 96° C. for 10 seconds (s), annealing at 45° C. for 5 seconds and extension at 60° C. for 4 minutes; then the sample was ramped to 95° C. and held for 3 minutes.

EXAMPLE 3

Loading Samples into the Reaction Portion of the Intake Capillaries of an Eight Channel System FIGS. 5A–5C show the steps to loading samples separately into the reaction portion 8 of the intake capillaries 3 and the purification columns before and after Sanger reactions. With MFTVs 17 closed and MFTVs 5 open, a 22 μL sample aliquot was aspirated into each intake capillary 3 from a microtiter plate 11 (not shown) where a row of 8 pre-mixed DNA sample templates and reagents were placed. Subsequently, a plug of 8.5 μL deionized water was loaded into each intake capillary 3 placing the sample aliquot into each reaction portion 8 in a hot-air thermal cycler 9. After opening MFTVs 17 and closing MFTVs 5, cycle sequencing reactions were initiated (FIG. 5A). During reaction, 1×TE buffer continuously flushed the purification columns at a flow rate of 20 μL/minute/channel from pump 18. After a reaction time of about 2.5 hours, MFTVs 17 were closed and MFTVs 5 were opened, so that 22.5 μL/channel was pulled into a TEFLON tubing region of the first manifold 15 (not shown) above the T-assembly 12 (not shown) (FIG. 5B).

MFTVs 5 were then closed and MFTVs 17 were opened, buffer flow direction was reversed transferring the reaction products into the purification columns 14a (FIG. 5C, not shown). Purification was performed at a flow rate of 20 μL/minute/channel with 1×TE buffer at the temperature was maintained at 60° C. by a hot water bath 28 (not shown). Purification was initiated by selecting the pump 19 at valve 21 (FIG. 3). To prepare the junctions 32 of the cross assembly 30 for injection, the temperature at the cross assembly 30 was set at 70° C. while deionized water flowed over the injection junction at 200 μL/minute/channel from the syringe pump 19. This continuous transverse flow of water at the proximal portion 97 (not shown) of the separation capillaries 34 caused dialysis at the interface of the sieving matrix and created a low ionic strength zone, thereby promoting stacking injection for pre-concentration of the analytes to be injected.

When the Sanger fragments reached the first detector 85 at point A 77, as recognized by the onset of a peak, electrokinetic injection to the separation capillaries was carried out at 150 V/cm for 2 minutes. When injection was completed, at about one-third of the peak height on its falling edge, MFTVs 17 were turned off and valve 21 was switched to select the syringe pump 19. 1 mL of 1×TBE buffer was used to remove residual deionized water and re-ionize the injection zone at a very low flow rate, about 100 μl/minute to avoid losing the injected fragments. The 1×TBE transverse flow was then programmed to 500 μL/minute/channel during electrophoretic separation at 150 V/cm. More importantly, the temperature at the injection region 91 (not shown) of the cross assembly 30 was lowered to room temperature quickly so as to restore ionic strength at junctions 32. MFTVs 17 were turned on and regeneration of the purification columns 14a and intake capillaries 3 proceeded after the electrophoresis current was stabilized (about 40 minutes).

The microreactor array 2 containing the intake capillaries 3 and reaction portions 8, the cross assembly 30 and the T-assembly 12 were regenerated by flushing with 0.2 M NaOH solution, 1×TE buffer, methanol and deionized water sequentially. The purification columns 14a were recovered by NaOH solution and 1×TE buffer. The syringe pump 19 was rinsed by two full strokes of water and the loading reagent whenever reagents were exchanged. These regeneration procedures were automated by controlling the syringe pump 19. The regeneration of the separation capillary array 33 was performed manually with a 100 μL syringe.

In the microreactor array 2, the variation in flow rates was determined by the difference in aspirated lengths of liquid plugs viewed outside the intake capillaries 3. It was determined that there existed about a 2% relative standard deviation among each individual channels. Therefore, it was determined that a 20 μL of reaction mixture occupies approximately 40±2.4 cm of reaction portion 8 of each intake capillary 3, the required distance between the proximal valve assemblies and the distal valve assemblies of MFTVs 5. Thus, a distance of approximately 7 cm was determined to be sufficient between the proximal and distal valve assemblies of MFTVs 5. It was determined that 30 μL of tubing between first manifold 15 and the T-assembly 12, was sufficient to guarantee independent sample manipulation in an 8 channel system. Thus, although 22.5 μL of a liquid plug is loaded into the tube region of the first manifold 15, only about 15 μL of a sample aliquot was injected into the chromatographic column array 14. The other 7 μL of deionized water was also loaded into the chromatographic column array 14 but there was no observable negative effects with respect to the purification and regeneration procedures.

Employing SEC columns packed with SEPHADEX in the column array, it was discovered that the main source of back pressure was due to the restricted channel spacing between the packed particles, not the inner diameter. Thus, if the back pressure of the individual channels are not identical, flow will favor the channels with the least flow resistance. As shown in Example 4, it was observed that in an 8 channel run starting from 8 DNA M13mp 18 samples, the resulting Sanger products had no retention in size-exclusion chromatography as the denser the column packing the smaller its void volume. This may balance out the higher back pressure and thus the lower flow rate. Moreover, sample arrival time at point A 77 (FIG. 3) can also be adjusted by manipulating the length of the second joining capillaries 29 positioned after the chromatographic column array 14.

Figure 6:
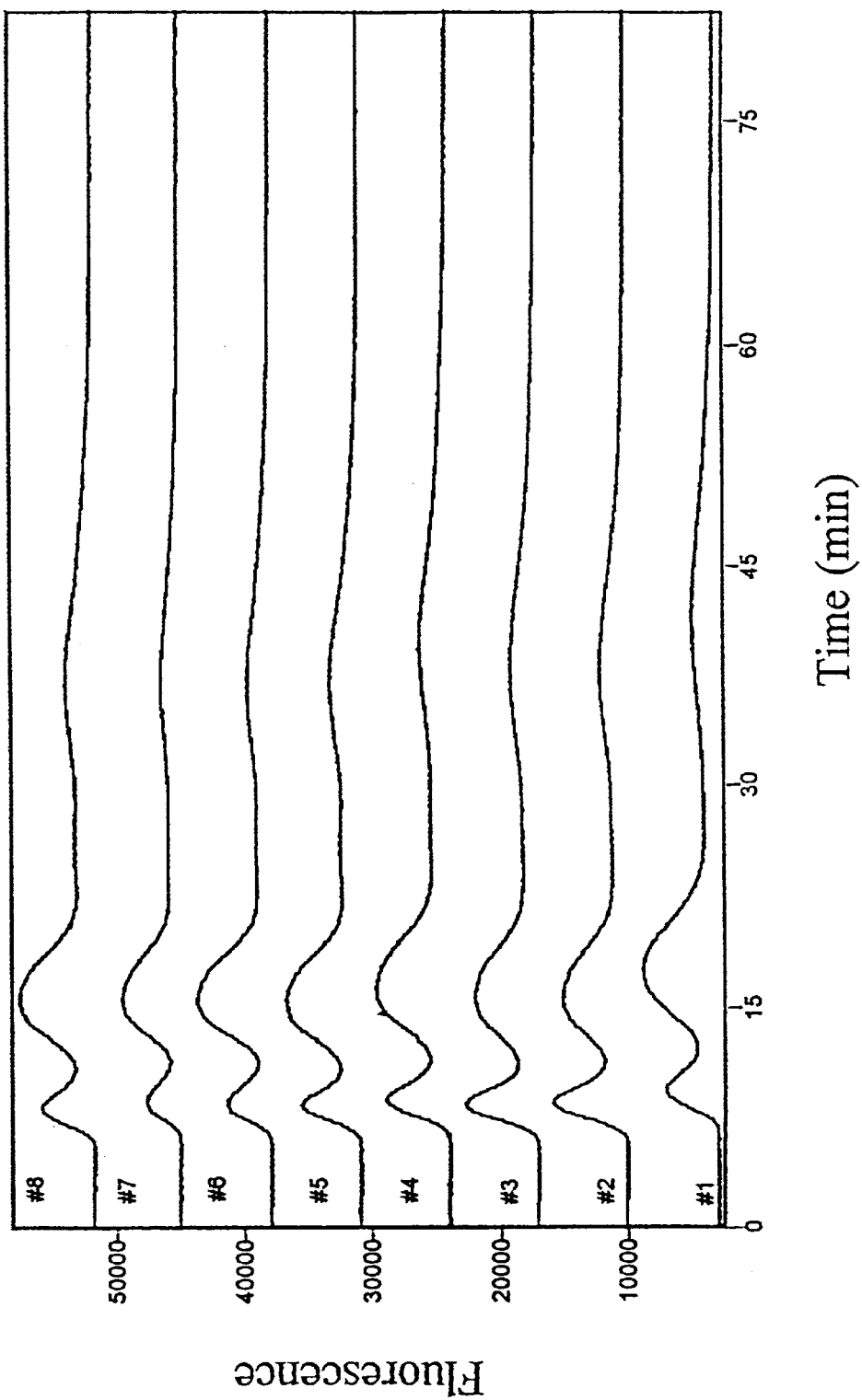
FIG. 6 shows simultaneous chromatograms for purification of cycle sequencing products.

FIG. 6, for example, shows the uniformity of elution monitored at point A 77 of FIG. 3. The total flow rate before first manifold 15 was 160 µL/minute. The fluorescence data was acquired through excitation of a 5 mW 514.5 nm Ar+ laser at 300 milliseconds (ms) exposure time with a CID detector after passing through a 610 nm long-pass filter. Second joining capillaries 29 that were 90 cm long and 100 micrometers (µm) i.d. were used to connect to each of the purification columns 14a. Thus, demonstrating that a synchronous "heart-cut" injection can be performed with careful engineering and relatively uniform packing of the purification columns 14a. Subsequently, once the system has been calibrated, only one of the purification columns 14a needs to be monitored at point A 77.

Figure 7:
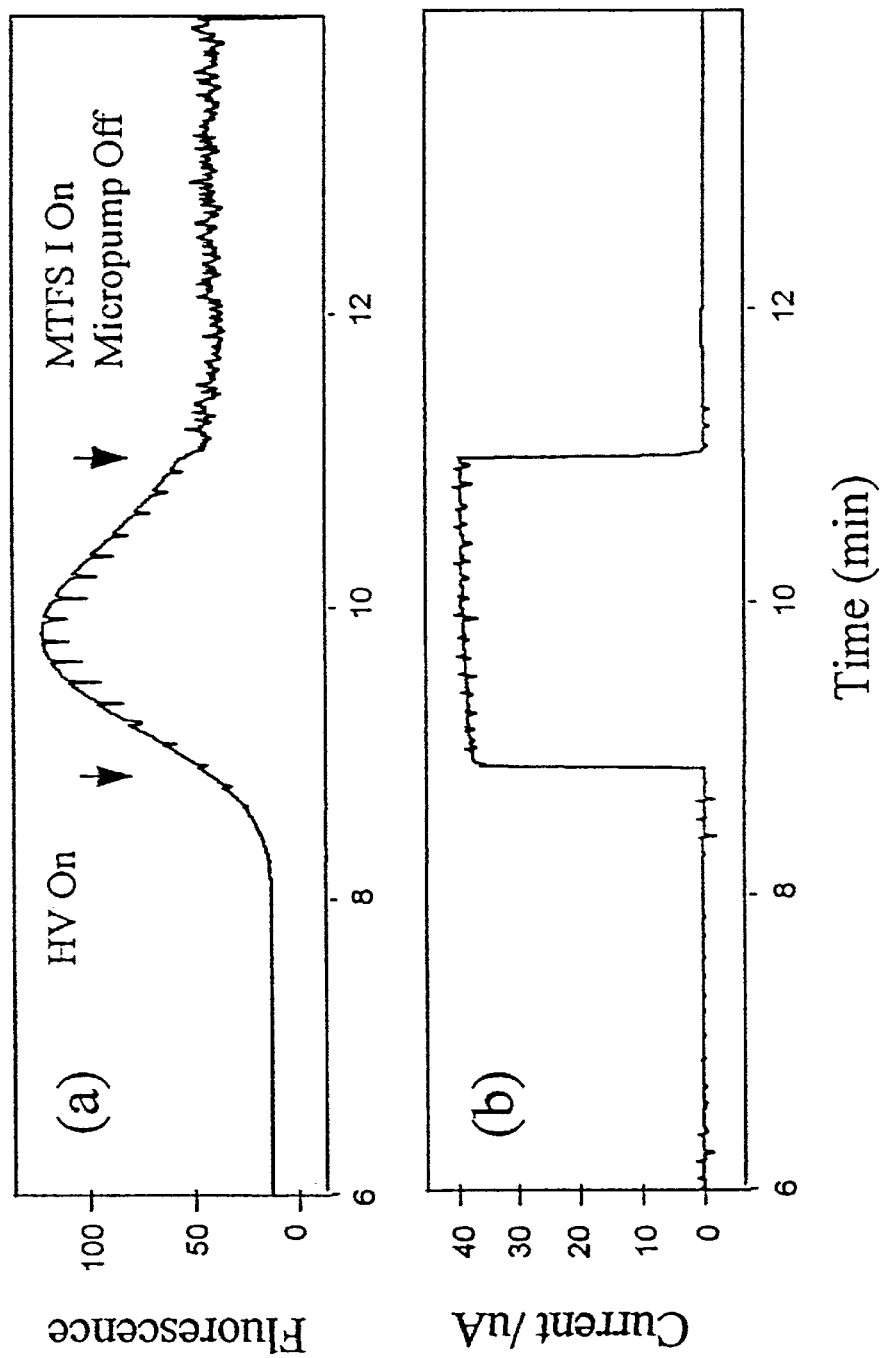
FIG. 7 is an illustration of a current-time profile for a "heart-cut" injection. Shown are both the signal from laser-induced fluorescence (a) and the total injection current response (b).

In reference to FIG. 7, upper panel (a) shows a chromatogram from one purification column and the signal from laser-induced fluorescence. The lower panel (b) shows the total current profile while performing a "heart-cut" injection. The observed regular spikes shown in FIG. 7 are due to pulsations from the micropump. Specifically, the peak width observed in FIG. 7 is about 3 minutes at 20 µL/minute/channel flow rate. From this, it is possible to estimate the dilution factor to be about 0.25. A 2-minute electrokinetic injection at the cross-junction will sample 96% of the eluting reaction plug. The DNA sample fragments, are focused at the entrance and the CE resolution is preserved. This phenomenon has been reported and used to pre-concentrate samples previously (Guttman et al., *Anal. Chem.* 67:2279–2283 (1995); Chien et al., *Anal. Chem.* 64:489A–496A)). In principle, asynchronous injection can be carried out by separately monitoring the DNA sample fragments in each channel, but this was ultimately found to be unnecessary and clearly simplifies expansion of the number of capillaries from 8 to 96 or even 1000. Back pressure also developed at the purification column array was less than 50 psi units per channel. With regard to the pressure, scale-up. to 96 or even 100 capillaries does not require higher pressure simply due to the proportional increase of the cross-sectional area. However, the pumps will have to have larger bores to handle the increased (total) liquid volume.

Depending on the samples selected for analysis and the analysis contained therein, the injection temperature must be optimized to denature the—sample at the cross-junction 30 without creating any air bubbles in the capillary. For samples, such as DNA that require heat to denature the Sanger fragments, this is particularly important. It was observed that with dITP cycle sequencing chemistry (Mizusawa et al., *Nucl. Acids Res.* 14:1319–1324 (1986), 70° C. works well for both denaturation and injection. With 7-deaze-dGTP chemistry (Barr et al., *BioTechniques* 4:428–432 (1986)), 90° C. was used for denaturation such that bubbles do not form during the capillary electrophoresis run and block the capillaries, although it allows for increased read length compared to dITP. As for multiplexing injection, an even temperature across the cross assembly is important. In contrast to a previous study (Tan et al., *Anal. Chem.* 69:664–674 (1997), it was discovered that it was not necessary to coat the cross-junctions with a BSA solution. This may be a result of differences in the geometry, surface, or material of the crosses employed. It is important to note that pressure was employed to control liquid flow at the cross junctions rather than electro-osmotic flow. This was necessitated by the presence of the purification columns in the chromatographic array. Finally, the various solutions employed to purify, rinse, run electrophoresis and recondition the components, may cause the nature of the surfaces to change over the course of system operation. Thus, electro-osmotic control of the system flow is not practical.

EXAMPLE 4

Analysis of 8 DNA Samples

Figure 8:
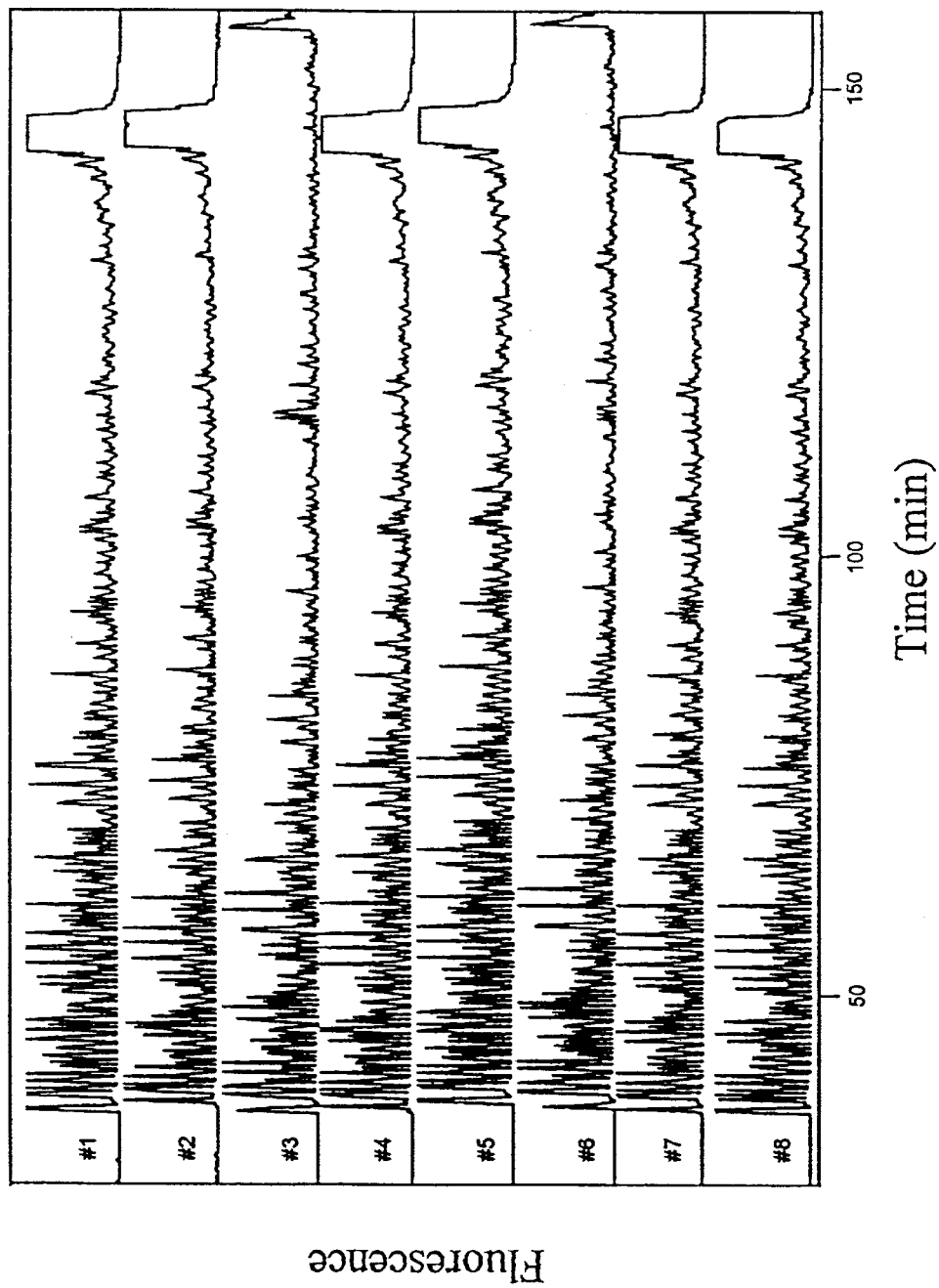
FIG. 8 illustrates electropherograms showing simultaneous sequencing of eight M13mp 18 DNA samples with the on-line integrated multiplexed system of the invention starting from samples.

FIG. 8 shows system performance of an 8 channel run starting from 8 DNA M13mp 18 samples. Individual separation capillaries 34 (not shown) in the separation capillary array 33 (not shown) are labeled from #1 to #8 according to proximity to the excitation laser 37 (not shown). The regular spikes shown in FIG. 8 are associated with pulsations from pump 18. Each electropherogram was normalized to the span of its panel in Gram/386 software (Galactic Industries, Salem, N.H.). The system parameters contained sample aliquots or "reaction plugs" that occupied 40 cm out of 77 cm of 250 µm i.d., and 360 µm o.d. fused-silica capillaries; the system flow rate was set at 20 µL/minute/channel; the purification columns 14a (not shown) were SEPHADEX G-25-50 columns set at 60° C.; the injection into each of the separation capillaries was a "heart-cut" injection performed at 70° C., with approximately 2 mL of water pre-conditioning, and the separation capillaries were 60 cm effective length of bare capillary filled with 1.5% high molecular weight PEO and a 1.4% low molecular weight mixture, 150 V/cm, and the detector employed was with CCD camera excitation: 15 mW 514.5 nm Ar ion laser with exposure time of 300 milliseconds.

As shown in FIG. 8, the absolute fluorescence intensities at the same base number decreased gradually with capillary number, e.g., 1–8. This is an inherent feature of side-entrance excitation geometry reported by Kambara (Anazawa et al., *Anal. Chem.* 68:2699–2704 (1996)) and Yeung (Lu et al., *Appl. Spectrosc.* 49:605–609 (1995)). It was observed, however, that much larger variations of intensities among individual capillary channels than reported by Kambara (Anazawa et al., *Anal. Chem.* 68:2699–2704 (1996)). The observed fluctuation, at least within respect to analysis of the 8 DNA M13mp 18 samples, was caused by heterogeneity in the efficiencies of individual sequencing reactions, efficiencies of the stacking injection and temporal variations in the "heart-cut" injection. The electropherograms of FIG. 8 also have very high signal to noise (S/N) ratios, as can be shown from the baselines before the primer peaks in FIG. 8. The S/N of the blue channel for capillary 8 is the lowest, but it is still 39 at 453 bases, which is clearly enough to call bases.

Figure 9:
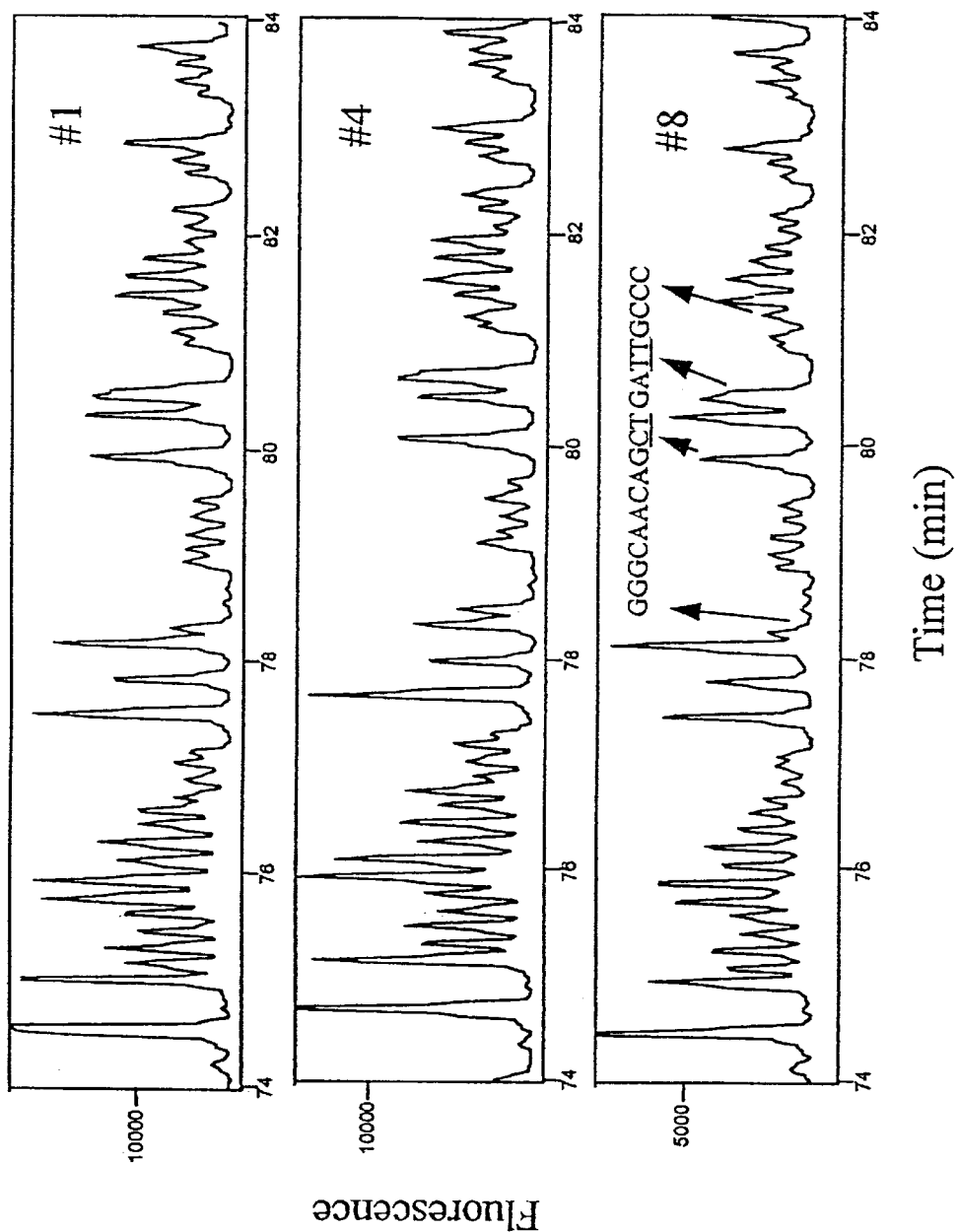
FIG. 9 shows the reproducibility of signal/noise ratio (S/N) and resolution in the separation capillary array.

The migration time and resolution of the DNA fragments in each separation capillary 34 (not shown) were not completely uniform among the 8 individual capillaries even for the best 3 channels as shown in FIG. 9. This result was probably attributable to several factors including the inhomogeneities in the separation gel matrix, small variations in capillary length, and reproducibility of the separation capillary regeneration and coating procedures. However, in sequencing DNA samples, each channel is an independent experiment and quantitative reproducibility is not required. Sequences for all 8 capillaries can be called based on the raw data up to 400 bases with an accuracy of 98%. The best capillary, e.g., number 5, produced this same level of accuracy out to 460 bases.

Figure 10:
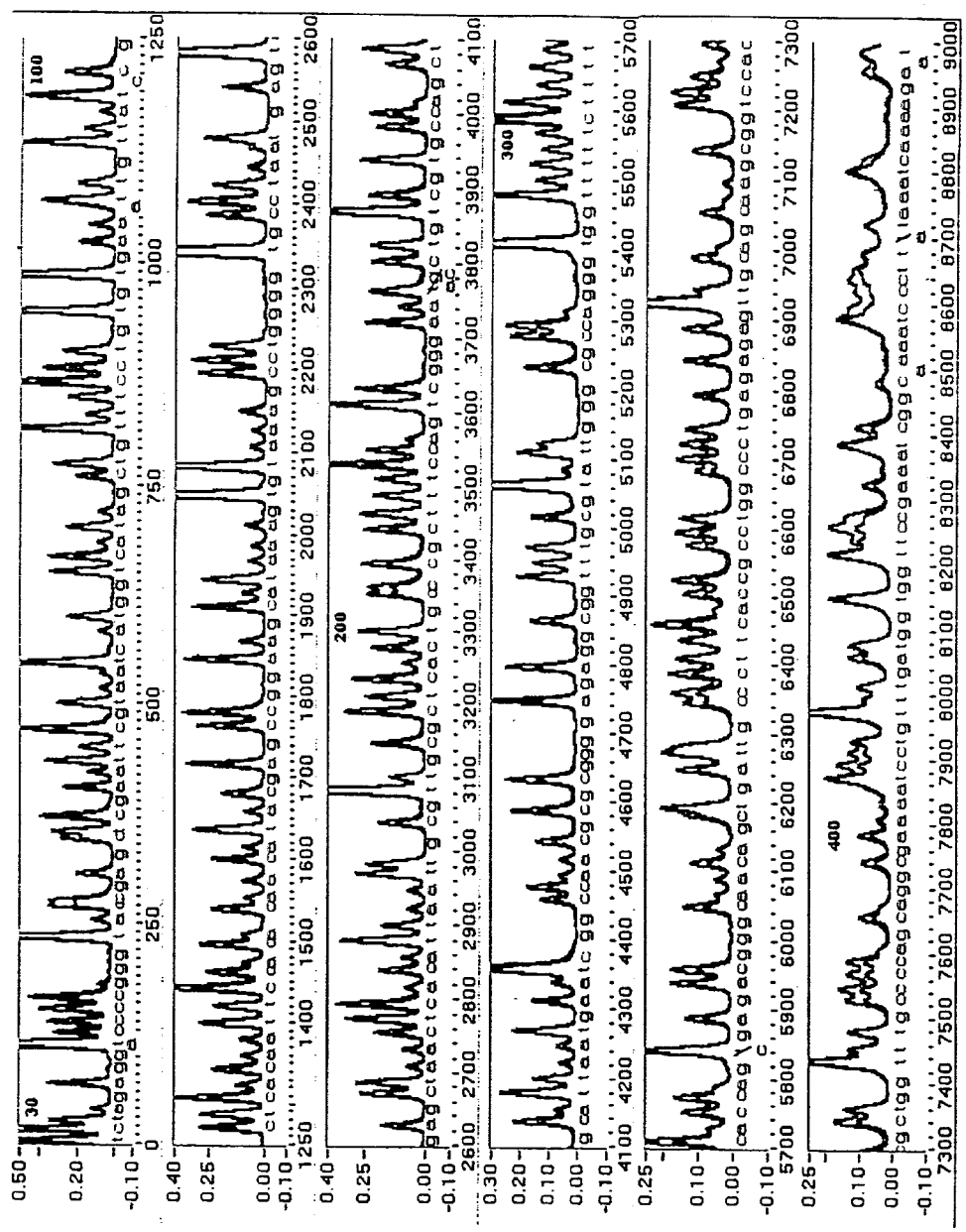
FIG. 10 represents the sequencing of M13mp 18 DNA from one separation capillary. The raw data from the blue and red channels are plotted. Base miscalls are corrected under the corresponding bases.

FIG. 10 shows the DNA sequence from capillary number 5 in the 8-capillary array. The y-axis is the relative fluorescence intensity normalized to the maximum peak in the electropherogram. The x-axis represents the migration time in terms of data points, starting at 37.2 minute for 0 and collected at 2.8 points/second. The low intensities of the G's (guanines) most likely due to the use of a 630 nm cutoff filter, poor enzyme incorporation rate and the lower ddGTP concentrations. The gaps between bases were corrected by an internally prepared software program to account for the weak G's. The last peaks, i.e., compression peaks, resolved at about 150 minutes with 60 cm effective capillary length and 150 V/cm. Notably, only about half the capillary length was necessary for separation. By employing better software and additional optimization of the sieving matrix and separation conditions, it should be possible to sequence 500 bases within an hour employing the present system.

The ability to recondition the system of the intention is an important factor. In reference to FIG. 1, it was observed that the same intake capillaries 3 in the microreactor array 2 and the same purification columns 14a in the chromatographic column array 14 were usable over a period of four months, performing more than 20 different sample runs with no significant degradation observed in system performance. Thus, although the reaction efficiency may vary from run to run and from capillary to capillary, it was not critical in sequencing the DNA samples as long as sufficient sequencing products were provided to maintain a minimum S/N.

Significantly, integrating and multiplexing the system did not add any extra requirements to the regeneration protocols. This is in contrast to what was previously demonstrated by Tan et al., *Anal. Chem.*, 69:664–674 (1997). However, multiplexing did add a small positive pressure to the separation capillaries 34 of the separation capillary array 33 due to the presence of a transverse buffer flow during electrophoresis. This was not a problem for integration with a single channel because the flow-gate interface was successfully employed even in capillary zone electrophoresis (Lemmo et al., *Anal. Chem.*, 65:1576–1581 (1993)). The difference in multiplexing, as opposed to a single channel system, is the need to produce uniform transverse flow rates among the individual capillaries, which requires a finite flow resistance at the waste outlet of the cross assembly. Thus, this requires that a relatively nonviscous sieving matrix may be disturbed by the flow to degrade the resolution.

The complete time for analysis of the 8 DNA M13mp 18 samples was about 5.5 hours including 2.5 hours for separation, 2.5 hours for reaction and about 0.5 hour for purification and sample loading. However, regeneration of the intake capillaries 3 can be done during separation and vice versa. Thus, with a slight modification of system operation described herein, one should be able to carry out sample reaction and electrophoretic separation at the same time. Furthermore, reaction time in the air thermal cycler can be as short as 25 minutes (Swerdlow et al., *BioTechniques* 512–519 (1993)). Additionally, reducing the separation time in the separation capillaries to 1 hour with 1000 bases sequenced has also been recently reported (Salos-Solano et al., *Eleventh International Symposium on High Performance Capillary Electrohoresis and Related Microscale Techniques,* Abstract P547 (1998)). Thus, producing 1.2 million bases of sequencing data per day per instrument could be achievable if the system is scaled up to 96 channels.

EXAMPLE 5

Assembly and Performance of MFTVs

Referring to FIGS. 2A and 2B, MFTVs 5, i.e, MFTVs 5a and MFTVs 5b, and MFTVs 17, were assembled on a ¼ inch (o.d.) stainless steel tube and eight small slots or holes with 0.03 inch diameter were opened on opposite sides of the center to allow the passage of 8 pieces of 0.028 inch (o.d.) and 0.016 inch (i.d.) stainless steel tubing from Small Parts, Inc., Miami Lakes, Fla., i.e., hypodermic tubes, were packed in parallel to prepare a hypodermic tubing array 101. This tubing array was welded onto the ¼ inch stainless steel tubing. After a small K type thermocouple 100, available from Omega, Stamford, Conn., was taped in the center of the array without having direct contact to the array, a heating tape 102, also available from Omega, Stamford, Conn., having 10 W/in$^2$ power density was wrapped around the ¼ inch stainless steel tubing and hypodermic tube array. A heat insulator 103 was placed outside the prepared assembly to prevent energy loss. This arrangement is shown in FIG. 2B.

A 250 μm i.d. and 360 μm o.d. fused-silica intake capillary 3 (not shown) passed through each of the hypodermic tubes. To turn off or close MFTVs 5 and MFTVs 17, the temperature was decreased to about −20° C. by opening cryogenic solenoid valves 80 and/or 81 (FIG. 1 (Valcor Scientific, Springfield, N.J.) and allowing liquid nitrogen to flow into the ¼ inch stainless steel tubing, thereby freezing a "plug" of solution inside each fused-silica capillary. To turn MFTVs 5 and MFTVs 17 on or open, the temperature was increased to about +20° C. through the heating tape 102 thereby thawing the solution plug. The turning on and off of any of these MFTV assemblies required 8 simultaneous phase transitions in each MFTV. The signal from the thermocouple goes through a thermocouple amplifier (OMNI-AMP-IV-13-115, Omega, Stamford, Conn.) and was converted into temperature after calibration. The temperature information, cryogenic valve and heating tape form an automatic loop controlled with Labview™ software.

The distal and proximal valve assemblies that make up MFTVs 5, are synchronized, such that the temperature monitored at the proximal valve assembly of MFTV 5 was used for feedback for the distal valve assembly of MFTV 5. The heaters 102 were controlled by the same relay. In view of this operation, the distal and proximal valve assemblies of MFTVs 5 can be considered as one 16-fold multiplexed on/off valve. Thus, MFTVs 17 and MFTVs 5 function independent of one and other.

To test the performance of each MFTV assembly, electrical currents for capillary electrophoresis were used as indicators (Guttman et al., *Anal. Chem.* 67:2279–2283 (1995); Chien et al., *Anal. Chem.* 64:489A–496A)). Four pieces of 80 cm long, 250 μm i.d. and 360 μm o.d. fused-silica intake capillaries filled with 1×TBE buffer under 10 kV were placed at the edge of distal valve assembly of MFTVs 5, a center portion the distal valve assembly of MFTV 5, the edge of the proximal valve assembly of MFTVs 5, and the edge of MFTVs 17, respectively. The current from each intake capillary 3 (not shown) was monitored through a 15-kW resistor.

It was observed that the response time on closing each MFTV assembly was about 20–25 seconds while the response time on opening a MFTV assembly was about 35–45 seconds. This response time was expected, as the response time for the initial closing of MFTV assemblies was always the longest because the inlet tubes need to be initially cooled down. Additionally, response time differences among the MFTV assemblies were relatively small, less than 1 second within the distal freeze thaw valve assembly of MFTV 5 and approximately 4 seconds between the distal and proximal freeze thaw valve assemblies that make up MFTVs 5.

EXAMPLE 6

Pumping and Regeneration System

Fifteen cm lengths of 0.02 inch (i.d.), ¹⁄₁₆ inch (o.d.) TEFLON tubing, approximately 30 μL, in each channel were used to connect the T-assembly 12 with first manifold 15. At the distal portion 6 of each of the intake capillaries 3 of the microreactor array 2, a holder was utilized to separate the intake capillaries 3 to form a line and to align the tip of each intake capillary 3 with the center of a row of a 96-well microtiter plate, which served as the delivery device 11. A 15 cm long, 0.03 inch (i.d.) and 1/16 inch (o.d.) TEFLON tube connected the first manifold 15 with an 8-position column-selection titanium valve 23 (Valco Instruments, Inc., Houston, Tex.).

As shown in FIG. 3, ports of valve 23 were connected to a waste line, a manual syringe and regeneration reagent reservoirs including deionized water, methanol, 1×TE buffer and 0.2 M NaOH solution. These reagents were used to regenerate both the microreactor array 2 and the purification columns 14a in the chromatographic array 14. The center port 24 of the 8-position valve 23 was coupled to a two-position sample-injection valve 21 (Rheodyne, Cotati, Calif.) through a 10 cm long, 0.03 inch (i.d.) and 1/16 inch (o.d.) TEFLON tube. One position of valve 21 was connected to a micropump 18 (Ultra-plus MicroLC System, Micro-Tech Scientific, Sunnyvale, Calif.) and the other to port 66 of a six-position selection valve 22. Port 67 of valve 22 was connected to a syringe pump 19 drive module (Kloehm Company, Inc., Las Vegas, Nev.) with a 1-mL syringe. Ports 55, 54, 53, and 56 of valve 22 were connected to the reservoirs of running buffer (1×TBE), deionized water, BSA solution, waste bottle. Port 57 was connected to center port 90 of the second manifold 26.

Purification columns 14a of the chromatographic array 14 were packed with size-exclusion media (Sephadex G-25-50, Supelco, Bellefonte, Pa.) as described in Tan et al., *Anal. Chem.* 69:664–674 (1997), except that the column frit was changed into an in-line filter from Upchurch Scientific (Oak Harbor, Wash.). The separation columns 14a were connected to the T-assembly 12 through 20 cm long, 150 $\mu$m (i.d.) and 360 $\mu$m (o.d.) fused-silica first joining capillaries 27. 100 $\mu$m (i.d.) and 360 $\mu$m (o.d.) fused-silica second joining capillaries 29 joined the separation columns 14a to the cross assembly 30 for injection into the separation capillary array 33. The lengths of the 100 $\mu$m (i.d.) capillaries varied between 50 and 60 cm for the individual channels so that the small difference in flow rates among channels could be compensated for. Most of the length of the 30-cm-long purification columns 14a (except their frits) were immersed in a hot water bath 28 (HB, Grant Instruments, Barrington Cambridge) which was pre-set at 60° C.

A 1mW 543.6 mn He—Ne laser 38 (Melles Griot, Irvine, Calif.) was used for monitoring the elution from one of the purification columns, shown as point A 77 in FIG. 1. The first detector 85 having an uncoated plano-convex lens 39 (Edmund Scientific, Barrington, N.J.) with 12-mm focal length was used to focus laser 38 to the capillary window at point A 77. A 10×microscope objective 40 (Edmund) was used to collect the fluorescence perpendicular to the excitation laser. A RG610 cutoff filter was employed to block the scattered light. A photomultiplier tube 41 (R928, Hamamatsu Corp., Bridgewater, N.J.) operating at 1000 V was used to generate an electrical signal. The signal was digitized at one of the analog input channels of a multifunctional data acquisition board (AT-MIO16DE-10, National Instruments, Austin, Tex.).

The cross assembly 30 was comprised of 8 PEEK cross junctions 32 (Upchurch Scientific), a heating tape (Omega), a themocouple (Omega), and eight aluminum rods, e.g., 1 inch diameter and 1/4 inch long, and one separate piece with the same diameter but 1.5 inches long. Each cross junction 32 was sandwiched in between two short aluminum rods, and the whole multi-layer sandwich was mounted on the long aluminum rod and a plastic holder. The heating tape simultaneously wrapped around all the aluminum rods so that they became 9 similar small heaters. The thermocouple was implanted in the center of this assembly. Meanwhile, an electrical fan can blow air into the whole assembly for cooling.

The four limbs of each separate junction 32 were respectively connected to a purification column 14a, second manifold 26, a separation capillary 34 and third manifold 31. The connection made to manifold 31 was through a short piece of 2 inch long, 0.03 inch (i.d.) and 1/16 inch (o.d.) stainless steel tube and a long piece of 12 cm long TEFLON tube with the same inner diameter. All the stainless steel tubes used were welded to a piece of copper wire, that functioned as the ground electrode during electrophoresis. The connections between second manifold 26 and manifold 31 were made as symmetrical as possible to provide uniform flow rates at each channel during the run. TEFLON tubing was also used to bring the waste stream from manifold 31 to a waste container. The cross assembly 30 was horizontally placed with second manifold 26 positioned at the bottom and manifold 31 positioned at the top.

EXAMPLE 7

DNA Separation and Detection in the Separation Capillary Array

As shown in FIG. 1, eight separation capillaries 34 with 75 $\mu$m i.d. and 360 $\mu$m o.d. were packed side-by-side. Transparent windows portions 93 were constructed by burning the polyimide coatings of each separation capillary with a micro-torch, removing burrs at both sides of the window with a blade, and clamping those between two flat surfaces of a plastic holder. A plastic holder was then mounted on a translational stage after adjusting and tilting the separation capillary array 33 to be parallel to an optical table. The distal portion 96 of each of the separation capillaries 34 were separately immersed into 1×TBE buffer while the proximal portions 97 of each separation capillary 34 were connected to cross assembly 30 by junctions 32.

The geometry for multiplexed excitation and detection utilized herein, was similar to the previous works by Kambara (Anazawa et al., *Anal. Chem.* 68:2699–2704 (1996)) and Yeung (Lu et al., *Appl. Spectrosc.* 49:605–609 (1995)) although minor modifications were made to further improve S/N ratios. 15 mW of 514.5 nm light from an air-cooled single-line argon-ion laser (Uniphase, Palo Alto, Calif.), after separating from its plasma emission by a 60° prism (Edmund Scientific), was focused on the first capillary of the array through a 40-millimeter (mm) focal length plano-convex lens (Edmund Scientific). The laser beam not only was co-planar with the capillary array but also had a 20° incident angle to the array at the first capillary in the array. The multiple laser focusing technique described by Kambara (Anazawa et al., *Anal. Chem.* 68:2699–2704 (1996)) was utilized herein, and is determined by observing the image spot of the laser after the array. The off-axis arrangement avoids collecting the dominant scattering ring into a CCD camera 36 to lower the background.

Fluorescence from DNA bands in each separation capillary 34 was monitored simultaneously with a cooled CCD camera 36 (Photometrics, Tucson, Ariz.) from a direction perpendicular to the separation capillary array 33 plane. The CCD camera had a lens (Canon, Japan, 70 mm dia. and 24 mm focal length) attached, two holographic notch-plus filters at 514.5 nm (Kaiser Optical System, Ann Arbor, Mich.) behind the lens, and an image-splitting filter set before the lens. The image-splitting filter set was made of a 630 nm long-pass filter (Edmund Scientific) and a quartz plate to compensate for the optical pathlength with a tilted angle. Two images were formed corresponding to each capillary with an image size of 7×3 pixels. The image from the 630-nm filter was called the "red" channel while the one from quartz plate was the "blue" channel (see FIG. 10). This two-color detection scheme has been reported previously (Tan et al., *Anal. Chem.* 69:664–674 (1997)). The exposure time of the camera was set at 300 ms, so the frame rate was about 3 Hz. Each frame contained two sub-arrays of pixels for both blue and red channels and were transferred into a host computer (Pentium 133 MHZ) during the exposure. Frames were accumulated into a raw data file by software written in C++. After the run, the raw data file was extracted into an ASCII file at the pixel corresponding to the center of each capillary. A base-calling program developed in Labview™ based on the histogram of four-label two-color ratios was then used to identify the sequence. Base calling is further described below.

75 $\mu$m i.d., 365 $\mu$m o.d. bare fused-silica capillaries (Polymicro Technologies, Phoenix, Ariz.), typically 80 cm long (60 cm effective length), were used as separation capillaries 34. The separation capillaries were flushed and coated with 2% of 1,000,000 MW polyvinylpyrrolidone (PVP) in 1×TBE buffer before filling with the sieving matrix. PEO was transferred and forced into the capillaries through a piece of 0.015 inch (i.d.) TEFLON tubing attached to 100-$\mu$L syringe from the detection end of each capillary. After running, the individual separation capillaries 34 were simply flushed with 0.1 M HCl solution and deionized water or pure methanol, and then coated with 2% of PVP solution again. A high-voltage power supply (Spellman, Plainview, N.Y.) was used to drive the electrophoresis from the anode at the detection end. Typically, 150 V/cm was used for both separation and injection of DNA Sanger fragments.

EXAMPLE 8

Automation and Control

As shown in FIG. 4, a Dell GXMT 5100 computer 20 (Dell Computer Corporation, Austin, Tex.) equipped with a multifunctional data acquisition board (AT-MIO-16DE-10, National Instruments, Austin, Tex.) and a 2-port serial interface board (AT-232/2, National Instruments) were used as control hardware while LABVIEW (National Instruments) was the programming platform for control software (FIG. 3). Two serial ports originated from the Dell computer and two additional ports from AT-232/2 board provided four communication channels through a standard RS-232 protocol. The communication channels were employed to control the syringe pump 19 (not shown) and its selection valve 22 (not shown), the micropump 18 (not shown), valve 23 (not shown), and 1/16 DIN temperature controller.

The temperature of the cross assembly 30 (not shown) was governed by the 1/16 DIN temperature controller through the heating tape, cooling fan and thermocouple. The analog input signals include the PMT for monitoring chromatographic elution, two thermocouples at each of the MFTV assemblies, and the total current of electrophoresis. Lines of digital I/O were connected to relays (ER/16, National Instruments) for controlling the cryogenic valves 10 (not shown), heating tapes for the each of the MFTV assemblies, heater for the SEC purification column array 14 (not shown), and the contact closure control of the sample injection valve 21 (not shown). A parallel cable was used to transfer the ASCII data files from the CCD host computer to the Dell computer for base calling. The system was completely controlled by the computer except for gel loading and operation of the hot-air thermal cycler 9 (not shown).

All patents, patent applications and publications are incorporated by reference herein as though individually incorporated by reference. While only certain preferred embodiments of this invention have been shown and described y way of illustration, many modifications will occur to those skilled in the art and it is therefore desired that it be understood that this is intended herein to cover all such modifications that fall with the scope of the invention.

What is claimed is:

1. An integrated multiplexed capillary electrophoresis system for analysis of an analyte in a sample comprising:
   a plurality of intake capillaries;
   a plurality of first junctions, each first junction in fluid communication with one of the plurality of intake capillaries;
   a first manifold in fluid communication with the first junctions;
   a chromatographic column array comprising a plurality of chromatographic columns having an outlet end, each chromatographic column in fluid communication with one of the plurality of first junctions;
   a first detector positioned to detect analytes eluting from the outlet ends of the chromatographic columns to determine whether the analyte arrival times are synchronous;
   a plurality of second junctions, each second junction in fluid communication with one of the plurality of chromatographic columns, the chromatographic columns being interposed between the first and second junctions;
   a second manifold in fluid communication with the second junctions; and
   a separation capillary array comprising a plurality of separation capillaries, each separation capillary in fluid communication with one of the plurality of second junctions and having an outlet end;
   the system having a first configuration wherein the chromatographic columns are in fluid communication with the intake capillaries and the separation capillaries and a second configuration wherein the chromatographic columns are in fluid communication with the first and second manifolds.

2. The system of claim 1 further comprising:
   a plurality of first freeze-thaw valves for regulating the flow of fluids in the system, each first freeze-thaw valve comprising a portion of an intake capillary;
   a plurality of first joining capillaries, each first joining capillary interposed between a first junction and a chromatographic column, the first junction being in fluid communication with the intake capillary; and
   a plurality of second freeze-thaw valves for regulating the flow of fluids in the system, each second freeze-thaw valve comprising a portion of a first joining capillary.

3. The system of claim 2 wherein at least one intake capillary comprises a reaction portion for reacting a sample.

4. The system of claim 3 wherein each of the plurality of first freeze-thaw valves comprises a distal freeze thaw valve comprising a portion of the intake capillary distal to the reaction portion and a proximal freeze-thaw valve comprising a portion of the intake capillary proximal to the reaction portion.

5. The system of claim 3 further comprising a heater assembly for heating the reaction portion of at least one of the plurality of intake capillaries.

6. The system of claim 3 wherein the reaction portion of at least one intake capillary comprises a loop.

7. The system of claim 1 wherein the first detector comprises an image array detector selected from the group consisting of a charge-coupled device and a charge-injection device.

8. The system of claim 1 wherein the separation capillary array comprises a plurality of parallel separation capillaries.

9. The system of claim 1 further comprising a second detector for detecting an analyte eluting from at least one separation capillary.

10. The system of claim 9 wherein the at least one separation capillary has a transparent window portion for detection of the analyte by the second detector.

11. The system of claim 1 further comprising a delivery device for introducing samples to at least one of the plurality of intake capillaries.

12. The system of claim 1 wherein the intake capillaries comprise fused-silica capillaries.

13. The system of claim 1 further comprising
a micropump for moving samples through the chromatographic column array and the separation capillary array, wherein the micropump is in fluid communication with each of the first manifold and the second manifold.

14. The system of claim 1 wherein the separation capillaries further comprise a polymer matrix.

15. The system of claim 14 wherein the polymer matrix is selected from the group consisting of poly(ethylene oxide), polyvinylpyrrolidone, polyacrylamide and polydimethylacrylamide.

16. The system of claim 1 wherein the plurality of intake capillaries comprises at least about eight intake capillaries.

17. The system of claim 1 wherein the plurality of intake capillaries comprises at least about ninety-six intake capillaries.

18. The system of claim 1 wherein the plurality of intake capillaries comprises at least about one thousand intake capillaries.

19. The system of claim 1 wherein each of the plurality of second junctions comprises a heating element.

20. A method for detecting an analyte in a plurality of samples comprising:
   (a) providing an integrated multiplexed capillary electrophoresis system comprising
      a plurality of intake capillaries, each intake capillary having an intake end;
      a plurality of first junctions, each first junction in fluid communication with one of the plurality of intake capillaries;
      a first manifold in fluid communication with the first junctions;
      a chromatographic column array comprising a plurality of chromatographic columns having an outlet end, each chromatographic column in fluid communication with one of the plurality of first junctions;
      a plurality of second junctions, each second junction in fluid communication with one of the plurality of chromatographic columns, the chromatographic columns being interposed between the first and second junctions;
      a second manifold in fluid communication with the second junctions; and
      a separation capillary array comprising a plurality of separation capillaries, each separation capillary in fluid communication with one of the plurality of second junctions and having an outlet end;
      the system having a first configuration wherein the chromatographic columns are in fluid communication with the intake capillaries and the separation capillaries and a second configuration wherein the chromatographic columns are in fluid communication with the first and second manifold;
   (b) introducing each of the plurality of samples into the inlet end of a different intake capillary;
   (c) transferring each of the plurality of samples from each intake capillary into a chromatographic column in fluid communication with each of the intake capillaries;
   (d) chromatographing each of the plurality of samples to yield a plurality of purified sample portions, the purified sample portions comprising at least one detectable analyte;
   (e) injecting each of the plurality of purified sample portions into a separation capillary in fluid communication with the chromatographic column;
   (f) separating each of the purified sample portions to yield a plurality of separated sample portions, each of the separated sample portions comprising at least one detectable analyte; and
   (g) detecting at least one detectable analyte.

21. The method of claim 20 wherein at least one of the intake capillaries further comprises a reaction portion.

22. The method of claim 21 further comprising a step prior to step (c) of reacting at least one of the plurality samples in the reaction portion of the intake capillary to yield a plurality of reacted samples, wherein each reacted sample comprises at least one detectable target species.

23. The method of claim 22 wherein the step of reacting at least one of the plurality of samples comprises heating the samples to yield reacted samples.

24. The method of claim 22 wherein the system further comprises:
   a plurality of first freeze-thaw valves for regulating the flow of fluids in the system, each first freeze-thaw valve comprising a distal freeze thaw valve comprising a portion of an intake capillary distal to the reaction portion of the intake capillary, and a proximal freeze thaw valve comprising a portion of the intake capillary proximal to the reaction portion of the intake capillary;
   a plurality of first joining capillaries, each first joining capillary interposed between a first junction and a chromatographic column, the first junction being in fluid communication with the intake capillary; and
   a plurality of second freeze-thaw valves for regulating the flow of fluids in the system, each second freeze-thaw comprising a portion of a first joining capillary;
   the method further comprising:
      prior to step (c), closing each of the plurality of distal and proximal freeze-thaw valves to isolate samples in the reaction portion of at least one of the intake capillaries;
      subsequent to step (c), opening each of the distal and proximal freeze-thaw valves to release reacted samples from the reaction portion of at least one of the intake capillaries; and concurrently closing the second plurality of freeze thaw valves so as to position the reacted samples in the first junction.

25. The method of claim 20 wherein the intake capillaries comprise fused-silica capillaries.

26. The method of claim 20 wherein the separation capillaries comprise a polymer matrix.

27. The method of claim 26 wherein the polymer matrix is selected from the group consisting of poly(ethylene oxide), polyvinylpyrrolidone, polyacrylamide and polydimethylacrylamide.

28. The method of claim 20 wherein the separation capillary array comprises at least about eight separation capillaries.

29. The method of claim 20 wherein the separation capillary array comprises at least about ninety-six separation capillaries.

30. The method of claim 20 wherein the separation capillary array comprises at least about one thousand separation capillaries.

31. The method of claim 20 wherein the chromatographic columns are selected from the group consisting of size-exclusion purification columns, ion-exchange columns, reverse-phase columns, hydrophobic columns, normal phase columns and affinity purification columns.

32. The method of claim 31 wherein the chromatographic columns are size-exclusion columns.

33. The method of claim 20 wherein step (d) further comprising detecting analytes eluting from the outlet ends of the chromatographic columns by a first detector to determine whether the analyte arrival times are synchronous.

34. The method of claim 33 wherein the first detector comprises an image array detector selected from the group consisting of a charge-coupled device and a charge-injection device.

35. The method of claim 20 wherein the separation capillary array comprises a plurality of parallel separation capillaries.

36. The method of claim 20 wherein step (g) further comprising detecting at least one separated analyte from at least one separation capillary by a second detector.

37. The method of claim 36 wherein at least one of the separation capillaries has a transparent window portion for detecting a separated analyte by the second detector.

38. The method of claim 20 comprising prior to step (f) the step of washing the chromatographic columns with a buffer.

39. The method of claim 38 wherein regeneration of chromatographic columns is performed concurrent with step (f).

40. The method of claim 20 wherein injection of the purified sample portions into each of the separation capillaries is maintained at a temperature of about 50° C. to about 90° C. during step (e).

41. The method of claim 20 wherein the detectable analyte is a fluorescent target species.

42. The method of claim 20 wherein the detectable target species comprises a nucleic acid.

43. The method of claim 20 further comprising heating the purified sample portions in each of the second junctions immediately prior to step (e).

44. A method for sequencing nucleic acids in a plurality of samples comprising:
  (a) providing an integrated multiplexed capillary electrophoresis system comprising
    a plurality of intake capillaries at least one intake capillary comprising a reaction portion for reacting a sample;
    a plurality of first junctions, each first junction in fluid communication with one of the plurality of intake capillaries;
    a first manifold in fluid communication with the first junctions;
    a chromatographic column array comprising a plurality of chromatographic columns having an outlet end, each chromatographic column in fluid communication with one of the plurality of first junctions;
    a plurality of second junctions, each second junction in fluid communication with one of the plurality of chromatographic columns, the chromatographic columns being interposed between the first and second junctions;
    a second manifold in fluid communication with the second junction;
    a separation capillary array comprising a plurality of separation capillaries, each separation capillary in fluid communication with one of the plurality of second junctions and having an outlet end;
    a plurality of first freeze-thaw valves for regulating the flow of fluids in the system, each first freeze-thaw valve comprising a portion of an intake capillary wherein each of the plurality of first freeze-thaw valves comprises a distal freeze thaw valve comprising a portion of the intake capillary distal to the reaction portion and a proximal freeze-thaw valve comprising a portion of the intake capillary proximal to the reaction portion;
    a plurality of first joining capillaries, each first joining capillary interposed between a first junction and a chromatographic column, the first junction being in fluid communication with the intake capillary;
    a plurality of second freeze-thaw valves for regulating the flow of fluids in the system, each second freeze-thaw comprising a portion of a first joining capillary;
  (b) introducing each of the plurality of samples into the reaction portion of a different intake capillary, each sample comprising a nucleic acid;
  (c) reacting each of the plurality of samples in a DNA sequencing reaction to yield a plurality of reacted samples, each reacted sample comprising a plurality of detectably labeled nucleic acid fragments having different lengths;
  (d) transferring each of the plurality of reacted samples from each of the intake capillaries into the chromatographic column in fluid communication with the intake capillary;
  (e) chromatographing each of the plurality of reacted samples to yield a plurality of purified samples, each purified sample comprising a plurality of detectably labeled nucleic acid fragments having different lengths;
  (f) injecting each of the plurality of purified samples into a separation capillary in fluid communication with the chromatographic column;
  (g) separating each of the plurality of purified samples to yield, for each purified sample, a plurality of separated detectably labeled nucleic acid fragments having different lengths;
  (h) detecting the detectably nucleic acid fragments having different lengths; and
  (i) for each sample, determining the sequence of the nucleic acid.

45. The method of claim 44 wherein the DNA sequencing reaction of step (c) is a labeled terminator cycle sequencing reaction.

46. The method of claim 44 further comprising heating the purified sample portions in each of the second junctions immediately prior to step (f).

* * * * *